United States Patent
O'Reilly et al.

(10) Patent No.: US 10,335,448 B2
(45) Date of Patent: Jul. 2, 2019

(54) COMPOSITIONS AND METHODS FOR INHIBITING FIBROSIS

(71) Applicant: The UAB Research Foundation, Birmingham, AL (US)

(72) Inventors: Philip J. O'Reilly, Hoover, AL (US); Edwin J. Blalock, Vestavia Hills, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 15/525,682

(22) PCT Filed: Nov. 10, 2015

(86) PCT No.: PCT/US2015/059980
§ 371 (c)(1),
(2) Date: May 10, 2017

(87) PCT Pub. No.: WO2016/077365
PCT Pub. Date: May 19, 2016

(65) Prior Publication Data
US 2017/0333517 A1    Nov. 23, 2017

Related U.S. Application Data

(60) Provisional application No. 62/077,569, filed on Nov. 10, 2014.

(51) Int. Cl.
| | |
|---|---|
| *A61K 38/06* | (2006.01) |
| *A61K 45/06* | (2006.01) |
| *G01N 33/68* | (2006.01) |
| *G01N 33/573* | (2006.01) |
| *A61P 43/00* | (2006.01) |
| *A61K 38/08* | (2019.01) |
| *A61K 38/10* | (2006.01) |
| *A61K 9/00* | (2006.01) |
| *C12Q 1/6883* | (2018.01) |

(52) U.S. Cl.
CPC .......... *A61K 38/06* (2013.01); *A61K 9/0043* (2013.01); *A61K 9/0053* (2013.01); *A61K 38/08* (2013.01); *A61K 38/10* (2013.01); *A61K 45/06* (2013.01); *C12Q 1/6883* (2013.01); *C12Y 304/15001* (2013.01); *G01N 33/573* (2013.01); *G01N 33/6893* (2013.01); *C12Q 2600/158* (2013.01); *G01N 2333/46* (2013.01); *G01N 2333/948* (2013.01); *G01N 2333/96433* (2013.01); *G01N 2333/96494* (2013.01); *G01N 2800/12* (2013.01); *G01N 2800/7052* (2013.01)

(58) Field of Classification Search
CPC ........ A61K 38/06; A61K 38/08; A61K 38/10; A61K 9/0043; A61K 45/06; A61K 9/0053; C12Y 304/15001; C12Q 1/6883; C12Q 2600/158; G01N 33/573; G01N 33/6893; G01N 2333/948; G01N 2333/96433; G01N 2333/96494; G01N 2800/7052; G01N 2333/46; G01N 2800/12

See application file for complete search history.

(56) References Cited

U.S. PATENT DOCUMENTS

2009/0311184 A1    12/2009    Yu

FOREIGN PATENT DOCUMENTS

| RU | 2403909 | 11/2010 | |
|---|---|---|---|
| WO | WO-2012106382 A1 * | 8/2012 | ........... A61K 9/0078 |
| WO | 2016077365 | 5/2016 | |

OTHER PUBLICATIONS

Overbeek et al, N-acetylated Proline-Glycine-Proline induced G-protein dependent chemotaxis of neutrophils is independent of CXCL8 release, European Journal of Pharmacology, 2011, 668, pp. 428-434.*
COPD vs Pulmonary Fibrosis: Here's What You Need to Know, from https://lunginstitute.com/blog/copd-vs-pulmonary-fibrosis-heres-what-you-need-to-know/, pp. 1-5, Jun. 23, 2016.*
Mandal, Types of Fibrosis, from http://www.news-medical.net/health/Types-of-Fibrosis.aspx, Jul. 3, 2014, pp. 1-3.*
Wynn et al, Mechanisms of fibrosis: therapeutic translation for fibrotic disease, Nature Medicine, 2012, 18, pp. 1028-1040.*
Rosenbloom et al, Strategies for anti-fibrotic therapies, Biochimica et Biophysica Acta, 2013, 1832, pp. 1088-1103.*
Wynn, Integrating mechanisms of pulmonary fibrosis, J. Exp. Med., 2011, 208, pp. 1339-1350.*
General Information About Pulmonary Fibrosis, from https://www.thoracic.org/patients/lung-disease-week/2011/pulmonary-fibrosis-week/general-information-about-pulmonary-fibrosis.php, 2011, pp. 1-3.*
Mohammadi-Karakani et al, Lisinopril ameliorates paraquat-induced lung fibrosis, Clinica Chimica Acta, 2006, 367, pp. 170-174.*
American Thoracic Society. Idiopathic Pulmonary Fibrosis: Diagnosis and Treatment. International Consensus Statement. American Thoracic Society (ATS), and the European Respiratory Society (ERS), Am. J. Respir. Crit. Care Med., vol. 161, No. 2, 2000, pp. 646-664.
Akthar et al., Matrikines are Key Regulators in Modulating the Amplitude of Lung Inflammation in Acute Pulmonary Infection, Nat. Commun., vol. 6, No. 8423, 2015, pp. 1-14.

(Continued)

*Primary Examiner* — Karlheinz R. Skowronek
*Assistant Examiner* — Li N Komatsu
(74) *Attorney, Agent, or Firm* — Kilpatrick Townsend & Stockton, LLP

(57) ABSTRACT

Provided herein are compositions and methods for treating or preventing fibrosis.

8 Claims, 15 Drawing Sheets
Specification includes a Sequence Listing.

(56) References Cited

OTHER PUBLICATIONS

Anderson et al., Human Neutrophils Employ the Myeloperoxidase-Hydrogen Peroxide-Chloride System to Convert Hydroxy-Amino Acids into Glycolaldehyde, 2-Hydroxypropanal, and Acrolein. A Mechanism for the Generation of Highly Reactive Alpha-Hydroxy and Alpha,Beta-Unsaturated Aldehydes by Phagocytes at Sites of Inflammation, J Gin Invest., vol. 99, No. 3, 1997, pp. 424-432.
Arnesen, Towards a Functional Understanding of Protein N-terminal Acetylation, PLoS Biol., vol. 9, No. 5, e1001074, 2011, pp. 1-5.
Ashcroft et al., Simple Method of Estimating Severity of Pulmonary Fibrosis on a Numerical Scale, J. Clin. Pathol., vol. 41, No. 4, 1988, pp. 467-470.
Baluk et al., Endothelial Gaps and Adherent Leukocytes in Allergen-Induced Early and Late-Phase Plasma Leakage in Rat Airways, Am J Pathol., vol. 152, No. 6, 1998, pp. 1463-1476.
Barnes, Inflammatory Mechanisms in Patients With Chronic Obstructive Pulmonary Disease, J Allergy Clin. Immunol., vol. 138, Issue 1, 2016, pp. 16-27.
Baumgartner et al., Cigarette Smoking: a Risk Factor for Idiopathic Pulmonary Fibrosis, Am J Respir. Crit. Care Med., vol. 155, No. 1, 1997, pp. 242-248.
Berg, Determination of 3- and 4-Hydroxyproline, Meth. Enzymol., vol. 82, 1982, pp. 372-398.
Bernstein et al., A Modern Understanding of the Traditional and Nontraditional Biological Functions of Angiotensin-Converting Enzyme, Pharmacol. Rev., vol. 65, No. 1, Jan. 2013, pp. 1-46.
Braber et al., Cigarette Smoke-Induced Lung Emphysema in Mice Is Associated With Prolyl Endopeptidase, An Enzyme Involved in Collagen Breakdown, Am J Physiol. Lung Cell Mol. Physiol., vol. 300, No. 2, 2011, pp. L255-L265.
Cavasin et al., Prolyl Oligopeptidase is Involved in Release of the Antifibrotic Peptide Ac-SDKP, Hypertension, vol. 43, No. 5, May 2004, pp. 1140-1145.
Chernov, Effectivnost Primeneniya Ingibitorov Angiotenzin Prevraschauschego Fermenta U Bolnykh Khronicheskoi Bolezniu Legkikh Pri Sochetanii Legochnoi I Arterialnoi Gipertenzii, Avtoreferat Dissertatsii K.M.N., 2005, pp. 4, 5, 21 and machine translation in English.
Conte et al., Effects of Thymosin B4 and Its N-Terminal Fragment Ac-SDKP on TGF-β-Treated Human Lung Fibroblasts and in the Mouse Model of Bleomycin-Induced Lung Fibrosis, Expert Opin Biol Ther., vol. 15, Suppl 1, 2015, pp. S211-S221.
Di Gennaro et al., The Leukotrienes: Immune-Modulating Lipid Mediators of Disease, Adv Immunol., vol. 116, 2012, pp. 51-92.
Djekic et al., Attacking the Multi-Tiered Proteolytic Pathology of COPD: New Insights From Basic and Translational Studies, Pharmacol Ther., vol. 121, No. 2, 2009, pp. 132-146.
Dransfield et al., Acquired Cystic Fibrosis Transmembrane Conductance Regulator Dysfunction in the Lower Airways in COPD, Chest, vol. 144, No. 2, 2013, pp. 498-506.
Esther et al., Mice Lacking Angiotensin-Converting Enzyme Have Low Blood Pressure, Renal Pathology, and Reduced Male Fertility, Lab Invest., vol. 74, No. 5, 1996, pp. 953-965.
Funk, Prostaglandins and Leukotrienes: Advances in Eicosanoid Biology, Science, vol. 294, No. 5548, Nov. 30, 2001, pp. 1871-1875.
Gaggar et al., A Novel Proteolytic Cascade Generates an Extracellular Matrix-Derived Chemoattractant in Chronic Neutrophilic Inflammation, J Immunol., vol. 180, No. 8, 2008, pp. 5662-5669.
Haddox et al., Bioactivity of Peptide Analogs of the Neutrophil Chemoattractant, N-Acetyl-Proline-Glycine-Proline, Invest Ophthalmol Vis Sci, vol. 40, No. 10, Sep. 1999, pp. 2427-2429.
Haeggstrom et al., Structure and Catalytic Mechanisms of Leukotriene A4 Hydrolase, Prostaglandins Other Lipid Mediat., vol. 83, Issue 3, May 2007, pp. 198-202.
Hahn et al., The Matrikine N-a-PGP Couples Extracellular Matrix Fragmentation to Endothelial Permeability, Sci Adv., vol. 1, No. 3, e1500175, 2015, pp. 1-10.
Hardison et al., Cigarette Smoke Enhances Chemotaxis via Acetylation of Proline-Glycine-Proline, Front Biosci (Elite Ed)., vol. 4, 2012, pp. 2402-2409.
Hardison et al., The Presence of a Matrix-Derived Neutrophil Chemoattractant in Bronchiolitis Obliterans Syndrome After Lung Transplantation, J Immunol., vol. 182, No. 7, 2009, pp. 4423-4431.
Hautamaki et al., Requirement for Macrophage Elastase for Cigarette Smoke-induced Emphysema in Mice, Science, vol. 277, No. 5334, 1997, pp. 2002-2004.
Helmer, Differentiation Between Two Forms of Angiotonin by Means of Spirally Cut Strips of Rabbit Aorta, Am J Physiol., vol. 188, No. 3, 1957, pp. 571-577.
Hinman et al., Angiotensin Convertase Activities in Human Alveolar Macrophages: Effects of Cigarette Smoking and Sarcoidosis, Science, vol. 205, Issue 4402, 1979, pp. 202-203.
Hogg et al., The Pathology of Chronic Obstructive Pulmonary Disease, Annu Rev Pathol., vol. 4, 2009, pp. 435-459.
Horowitz et al., Mesenchymal Cell Fate and Phenotypes in the Pathogenesis of Emphysema, COPD., vol. 6, No. 3, Jun. 2009, pp. 201-210.
Houghton et al., Elastin Fragments Drive Disease Progression in a Murine Model of Emphysema, J Clin Invest., vol. 116, No. 3, 2006, pp. 753-759.
Jaspard et al., Differences in the Properties and Enzymatic Specificities of the Two Active Sites of Angiotensin I-converting Enzyme (Kininase II), Studies With Bradykinin and Other Natural Peptides, J Biol Chem., vol. 268, No. 13, 1993, pp. 9496-9503.
Junot et al., RXP 407, A Selective Inhibitor of the N-Domain of Angiotensin I-Converting Enzyme, Blocks in Vivo the Degradation of Hemoregulatory Peptide Acetyl-Ser-Asp-Lys-Pro with no Effect on Angiotensin I Hydrolysis, J. Pharmacol. Exp. Ther., vol. 297, No. 2, 2001, pp. 606-611.
Keogh et al., Angiotensin II Antagonism Fails to Ameliorate Bleomycin-Induced Pulmonary Fibrosis in Mice, Eur Respir J., vol. 25, No. 4, 2005, pp. 708-714.
Khalil et al., Macrophage Production of Transforming Growth Factor Beta and Fibroblast Collagen Synthesis in Chronic Pulmonary Inflammation, J Exp. Med., vol. 170, No. 3, Sep. 1989, pp. 727-737.
Konigshoff et al., The Angiotensin II Receptor 2 Is Expressed and Mediates Angiotensin Ii Signaling in Lung Fibrosis, Am J Respir. Cell Mol. Biol., vol. 37, No. 6, 2007, pp. 640-650.
Lentz et al., The Amino Acid Composition of Hypertensin II and Its Biochemical Relationship to Hypertensin I, J Exp. Med., vol. 104, No. 2, 1956, pp. 183-191.
Li et al., Angiotensin-Converting Enzyme N-Terminal Inactivation Alleviates Bleomycin-Induced Lung Injury, Am J Pathol., vol. 177, No. 3, Sep. 2010, pp. 1113-1121.
Li et al., Essential Roles for Angiotensin Receptor AT1a in Bleomycin-induced Apoptosis and Lung Fibrosis in Mice, Am J Pathol., vol. 103, No. 3, Dec. 2003, pp. 2523-2530.
Li et al., Extravascular Sources of Lung Angiotensin Peptide Synthesis in Idiopathic Pulmonary Fibrosis, Am J Physiol. Lung Cell Mol. Physiol., vol. 291, No. 5, 2006, pp. L887-L895.
Matsusaka et al., The Renin Angiotensin System and Kidney Development, Annu. Rev Physiol., vol. 64, 2002, pp. 551-561.
Michaud et al., Substrate Dependence of Angiotensin I-Converting Enzyme Inhibition: Captopril Displays a Partial Selectivity for Inhibition of N-Acetyl-Seryl-Aspartyl-Lysyl-Proline Hydrolysis Compared with that of Angiotensin I, Mol Pharmacol., vol. 51, No. 6, 1997, pp. 1070-1076.
Molina-Molina et al., Losartan Attenuates Bleomycin Induced Lung Fibrosis by Increasing Prostaglandin E2 Synthesis, Thorax, vol. 61, No. 7, 2006, pp. 604-610.
Ninomiya et al., Serum Angiotensin Converting Enzyme Activity in Ex-Smokers, Clin. Chem. Acta., vol. 164, No. 2, 1987, pp. 223-226.
O'Reilly et al., Angiotensin-Converting Enzyme Defines Matrikine-Regulated Inflammation and Fibrosis, JCI Insight, vol. 2, No. 2, Nov. 16, 2017, pp. 1-18.
O'Reilly et al., N-Alpha-PGP and PGP, Potential Biomarkers and Therapeutic Targets for COPD, Respir Res., vol. 10, No. 1:38, 2009, pp. 1-8.

(56) References Cited

OTHER PUBLICATIONS

O'Reilly et al., Neutrophils Contain Prolyl Endopeptidase and Generate the Chemotactic Peptide, PGP, From Collagen, J Neuroimmunol., vol. 217, No. 1-2, Dec. 10, 2009, pp. 51-54.
O'Reilly et al., Sputum PGP Is Reduced by Azithromycin Treatment in Patients With COPD and Correlates With Exacerbations, BMJ Open., vol. 3, No. 12, e004140, 2013, pp. 1-6.
Pauwels et al., Global Strategy for the Diagnosis, Management, and Prevention of Chronic Obstructive Pulmonary Disease. NHLBI/WHO Global Initiative for Chronic Obstructive Lung Disease (GOLD) Workshop Summary, Am J Respir Crit Care Med., vol. 163, No. 5, 2001, pp. 1256-1276.
International Application No. PCT/US2015/059980, International Preliminary Report on Patentability, dated May 26, 2017, 7 pages.
International Application No. PCT/US2015/059980, International Search Report and Written Opinion, dated Jan. 28, 2016, 9 pages.
Pittet et al., TGF-Beta Is a Critical Mediator of Acute Lung Injury, J Clin Invest., vol. 107, No. 12, Jun. 2001, pp. 1537-1544.
Rabe et al., Global Strategy for the Diagnosis, Management, and Prevention of Chronic Obstructive Pulmonary Disease: GOLD Executive Summary, Am J Respir Crit Care Med., vol. 176, Issue 6, 2007, pp. 532-555.
Raghu et al., An Official ATS/ERS/JRS/ALAT Statement: Idiopathic Pulmonary Fibrosis: Evidence-Based Guidelines for Diagnosis and Management, Am J Respir Crit Care Med., vol. 183, No. 6, 2011, pp. 788-824.
Rasoul et al., Antifibrotic Effect of Ac-SDKP and Angiotensin-converting Enzyme Inhibition in Hypertension, J Hypertens., vol. 22, No. 3, Mar. 2004, pp. 593-603.
Rennard et al., Cigarette Smoke Inhibits Alveolar Repair: a Mechanism for the Development of Emphysema, Am Thorac Soc., vol. 3, No. 8, 2006, pp. 703-708.
Rieger et al., Involvement of Human Plasma Angiotensin I-Converting Enzyme in the Degradation of the Haemoregulatory Peptide N-Acetyl-Seryl-Aspartyl-Lysyl-Proline, Biochem J., vol. 296, Dec. 1, 1993, pp. 373-378.
Rousseau et al., The Hemoregulatory Peptide N-Acetyl-Ser-Asp-Lys-Pro Is a Natural and Specific Substrate of the N-terminal Active Site of Human Angiotensin-Converting Enzyme, J Biol Chem., vol. 270, No. 8, 1995, pp. 3656-3661.
Sayed-Tabatabaei et al., A Study of Gene—Environment Interaction on the Gene for Angiotensin Converting Enzyme: a Combined Functional and Population Based Approach, J Med Genet., vol. 41, No. 2, 2004, pp. 99-103.
Sentandreu et al., A Fluorescence-based Protocol for Quantifying Angiotensin-Converting Enzyme Activity, Nat Protoc., vol. 1, No. 5, 2006, pp. 2423-2427.
Shapiro et al., Neutrophil Elastase Contributes to Cigarette Smoke-Induced Emphysema in Mice, Am J Pathol., vol. 163, No. 6, 2003, pp. 2329-2335.
Skeggs et al., The Preparation and Function of the Hypertensin-Converting Enzyme, J Exp Med., vol. 103, No. 3, 1956, pp. 295-299.
Snelgrove et al., A Critical Role for LTA4H in Limiting Chronic Pulmonary Neutrophilic Inflammation, Science, vol. 330, No. 6000, Oct. 1, 2010, pp. 90-94.
Snelgrove, Leukotriene A4 Hydrolase: An Anti-inflammatory Role for a Proinflammatory Enzyme, Thorax, vol. 66, No. 6, 2011, pp. 550-551.
Snelgrove et al., Targeting of a Common Receptor Shared by Cxcl8 and N-ac-pgp as a Therapeutic Strategy to Alleviate Chronic Neutrophilic Lung Diseases, Eur. J. Pharmacol., vol. 667, No. 1-3, Sep. 30, 2011, pp. 1-5.

Soubrier et al., Two Putative Active Centers in Human Angiotensin I-converting Enzyme Revealed by Molecular Cloning, Proc Natl Acad Sci USA, vol. 85, No. 24, 1988, pp. 9386-9390.
Ten Hoeve et al., Proline-Glycine-Proline as a Potential Biomarker in Chronic Obstructive Pulmonary Disease and Cystic Fibrosis, Tanaffos, vol. 11, No. 2, 2012, pp. 12-15.
Uchida et al., Acrolein Is a Product of Lipid Peroxidation Reaction. Formation of Free Acrolein and Its Conjugate With Lysine Residues in Oxidized Low Density Lipoproteins, J Biol Chem., vol. 273, No. 26, 1998, pp. 16058-16066.
Uhal et al., Angiotensin Signalling in Pulmonary Fibrosis, Int. J Biochem. Cell Biol., vol. 44, No. 3, Mar. 2012, pp. 465-468.
Van Houwelingen et al., Induction of Lung Emphysema Is Prevented by L-Arginine-Threonine-Arginine, FASEB J., vol. 22, No. 9, 2008, pp. 3403-3408.
Varland et al., N-Terminal Modifications of Cellular Proteins: The Enzymes involved their Substrate Specificities and Biological Effects, Proteomics, vol. 15, No. 14, 2015, pp. 2385-2401.
Vestweber, How Leukocytes Cross the Vascular Endothelium, Nat Rev Immunol., vol. 15, No. 11, 2015, pp. 692-704.
Wang et al., Human Lung Myofibroblast-Derived Inducers of Alveolar Epithelial Apoptosis Identified as Angiotensin Peptides, Am J Physiol., vol. 277, No. (6Pt 1), 1999, pp. LI158-L1164.
Weathington et al., A Novel Peptide CXCR Ligand Derived From Extracellular Matrix Degradation During Airway Inflammation, Nat Med., vol. 12, No. 3, 2006, pp. 317-323.
Weber et al., Myofibroblast-Mediated Mechanisms of Pathological Remodelling of the Heart, Nat Rev Cardiol., vol. 10, No. 1, Jan. 2013, pp. 15-26.
Wei et al., Expression and Characterization of Recombinant Human Angiotensin I-converting Enzyme. Evidence for a C-Terminal Transmembrane Anchor and for a Proteolytic Processing of the Secreted Recombinant and Plasma Enzymes, J Biol Chem., vol. 266, No. 9, 1991, pp. 5540-5546.
Wei et al., The Two Homologous Domains of Human Angiotensin I-converting Enzyme Are Both Catalytically Active, J Biol Chem., vol. 266, No. 14, 1991, pp. 9002-9008.
Wei et al., The Two Homologous Domains of Human Angiotensin I-converting Enzyme Interact Differently With Competitive Inhibitors, J Biol. Chem., vol. 267, No. 19, 1992, pp. 13398-13405.
Wells et al., A Randomized, Placebo-Controlled Trial of Roflumilast. Effect on Proline-Glycine-Proline and Neutrophilic Inflammation in Chronic Obstructive Pulmonary Disease, Am J Respir. Crit. Care Med., vol. 192, No. 8, 2015, pp. 934-942.
Wells et al., An Aberrant Leukotriene A4 Hydrolase-Proline-Glycine-Proline Pathway in the Pathogenesis of Chronic Obstructive Pulmonary Disease, Am J Respir Crit Care Med., vol. 190, No. 1, 2014, pp. 51-61.
Woodcock et al., The Treatment of Idiopathic Pulmonary Fibrosis, F1000Prime Rep., vol. 6, No. 16, Mar. 3, 2014, pp. 1-9.
Xu et al., A New Antifibrotic Target of Ac-SDKP: Inhibition of Myofibroblast Differentiation in Rat Lung With Silicosis, PLoS One, vol. 7, No. 7, e40301, Jul. 2012, pp. 1-11.
Xu et al., A Self-Propagating Matrix Metalloprotease-9 (MMP-9) Dependent Cycle of Chronic Neutrophilic Inflammation, PLoS One, vol. 6, Issue 1, e15781, 2011, pp. 1-12.
Yao et al., Losartan Attenuates Bleomycin-Induced Pulmonary Fibrosis in Rats, Respiration, vol. 73, No. 2, 2006, pp. 236-242.
Zaman et al., Drugs Targeting the Renin-Angiotensin-Aldosterone System, Nat Rev Drug Discov., vol. 1, No. 8, 2002, pp. 621-636.
Zou et al., Abeta42-to-Abeta40- and Angiotensin-Converting Activities in Different Domains of Angiotensin-Converting Enzyme, J Biol Chem., vol. 284, No. 46, Nov. 13, 2009, pp. 31914-31920.

* cited by examiner

COMPOSITIONS AND METHODS FOR INHIBITING FIBROSIS

CROSS REFERENCE TO RELATED APPLICATIONS

This application is a U.S. national stage application under 35 U.S.C. § 371 of PCT/US2015/059980, filed Nov. 10, 2015, which claims the benefit of U.S. Provisional Application No. 62/077,569, filed Nov. 10, 2014, which is hereby incorporated herein in their entirety by this reference.

STATEMENT REGARDING FEDERALLY FUNDED RESEARCH

This invention was made with government support under grant number HL092296 and HL07783 awarded by the National Institutes of Health. The government has certain rights in the invention.

BACKGROUND

Fibrosis is the formation of excess fibrous tissue in an organ or tissue, often as a reaction to inflammation or tissue injury. Pathological fibrosis is characterized by non-resolving or progressive tissue remodeling, which itself can cause tissue damage and organ failure.

SUMMARY

Provided herein is a method for reducing or preventing fibrosis in a subject. The method includes the steps of selecting a subject with or at risk for fibrosis and administering a therapeutically effective amount of a proline-glycine-proline (PGP)-containing peptide to the subject.

Further provided is a method of treating fibrosis or a disease associated with fibrosis in a subject. The method includes the steps of obtaining a biological sample from the subject; determining the level of expression or activity of angiotension-converting enzyme (ACE), Ac-PGP, PGP, prolyl endopeptidase (PE) and/or a matrix metalloprotease (MMP) in the sample. An increase in expression or activity of enzyme (ACE), a decrease in expression or activity of Ac-PGP, a decrease in expression or activity of PGP, a decrease in expression or activity of PE and/or a decrease in expression or activity of the MMP as compared to a control indicates the subject has fibrosis or a disease associated with fibrosis; and administering a therapeutically effective amount of a PGP-containing peptide to the subject.

Also provided herein is a composition comprising a therapeutically effective amount of a PGP-containing peptide and a pharmaceutical carrier.

DESCRIPTION OF DRAWINGS

FIGS. 2A-D: n=12 per group, FIG. 2E: n=4 per group, mean±SEM, *p≤0.05.

FIG. 9C shows that Ac-PGP degrading activity of BALF 7 days after bleomycin exposure was greater than control (*p≤0.01). The difference at 3 days was not significant. FIG. 9D shows that Captopril (1 µM) abolished Ac-PGP breakdown by 3 and 7 day bleomycin BALF (*p≤0.05 compared to without captopril). FIG. 9E shows that ACE activity and Ac-PGP breakdown correlate in BALF (n=10). FIG. 9F shows that macrophages increase dramatically in BALF by day 7 after bleomycin exposure (*p≤0.01 compared to PBS and 3 day bleomycin). Data presented as mean±SD, n=3-4 mice per group.

DESCRIPTION

Figure 1:
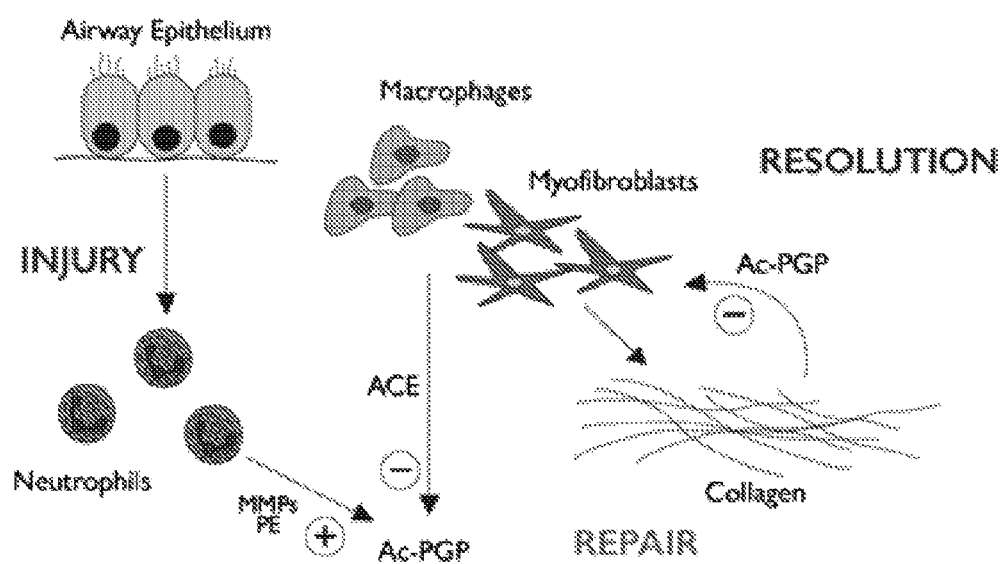
FIG. 1 is a schematic showing the effect of acute lung injury. In acute lung injury, neutrophils generate Ac-PGP from collagen to propagate inflammation. Ac-PGP inhibits myofibroblasts (MF) and must be cleared by macrophages and myofibroblast-derived angiotensin converting enzyme (ACE) to allow repair to start. Clearance of Ac-PGP by ACE helps prevent chronic inflammation and the pathologic fibrosis that accompanies it. During resolution, Ac-PGP is generated from newly-synthesized collagen, likely by myofibroblasts, and ACE activity diminishes. Ac-PGP feedback inhibits myofibroblasts and prevents further collagen deposition. In this way, ACE and Ac-PGP orchestrate repair. Perturbations of this pathway can lead to disease: too little Ac-PGP and too much ACE causing excess fibrosis as in idiopathic pulmonary fibrosis (IPF) and the opposite causing loss of matrix as in COPD.

Fibrosis is a stereotypical reaction to tissue injury. A common mechanism of pathological fibrosis is the persistent activation of tissue myofibroblasts. In the lung, fibrosis involving the airways, vasculature, alveoli and pleura can contribute to the progression of chronic lung diseases including asthma, chronic obstructive pulmonary disease (COPD), primary pulmonary hypertension, scleroderma and idiopathic pulmonary fibrosis (IPF). Neutrophils entering the lung generate the neutrophil-specific matrikine, proline-glycine-proline (PGP) from collagen. The initial cleavage of collagen is catalyzed by matrix metalloproteases (MMPs)-8 and 9, followed by prolyl endopeptidase (PE) which generates PGP. PGP is N-terminally acetylated by an unknown mechanism to generate N-acetyl (Ac)-PGP which is several times more potent (Haddox et al. "Bioactivity of peptide analogs of the neutrophil chemoattractant, N-acetyl-proline-glycine-proline. *Invest Ophthalmol Vis Sci* 40:2427-2429 (1999). PGP and Ac-PGP bind to CXC receptors on neutrophils and are biomarkers for lung diseases such as chronic obstructive pulmonary disease (COPD) and cystic fibrosis (CF). Therapies that effectively target pathological fibrosis are lacking, leading to poor outcomes.

Provided herein are methods of treating or preventing fibrosis. For example, provided herein is a method for reducing or preventing fibrosis in a subject, comprising selecting a subject with or at risk for fibrosis; and administering a therapeutically effective amount of a proline-glycine-proline (PGP)-containing peptide to the subject.

As used throughout, fibrosis is the development of excess fibrous connective tissue as a reparative response to injury or damage. This process can be pathological, reactive or benign. Fibrosis can refer to both the connective tissue deposition that occurs as part of normal healing as well as the excess tissue deposition that occurs as a pathological process. Fibrosis can be associated with one or more diseases. In the lung, fibrosis involving the airways, vasculature, alveoli and pleura can contribute to the progression of chronic lung or pulmonary diseases including asthma, chronic obstructive pulmonary disease (COPD), primary pulmonary hypertension, scleroderma and idiopathic pulmonary fibrosis (IPF). Other examples of fibrosis that occur in response to inflammation or damage are liver cirrhosis, fibrosis of the heart, mediastinal fibrosis, retroperitoneal fibrosis and myelofibrosis, to name a few.

In the methods provided herein, one of skill in the art would know how to select a subject with or at risk for fibrosis. For example, the subject could be a subject that has been diagnosed with fibrosis or the risk of fibrosis. The subject can also be a subject that has been diagnosed with a disease associated with fibrosis, could have a genetic propensity to fibrosis, or could have been exposed to environmental stimuli that cause fibrosis. The subject could have inhaled a caustic agent such as smoke or chemicals. The subject could be at post-operations risk for fibrosis. The subject could have been exposed to any variety of physical agents and injury (e.g., burns). Fibrosis or the risk of fibrosis can be detected in a human subject by, for example, detecting absent or decreased levels of Ac-PGP or PGP in lung samples, as compared to a control. The sample can be, for example, sputum, bronchoalveolar lavage fluids, biopsy (e.g. lung tissue or lung cells isolated from lung tissue). Alternatively, risk of fibrosis could be determined by detecting decreased or absent levels of enzymes responsible for generating Ac-PGP from collagen (for example, prolyl endopeptidase), or increased levels of enzymes responsible for degrading Ac-PGP, for example, angiotensin converting enzyme (ACE). As used throughout, a control can be a subject or a sample from a subject without fibrosis or risk for fibrosis. The control can also be a subject or a sample from a subject that has been successfully treated for fibrosis. The control can also be a known reference sample or value.

One or more symptoms of fibrosis can also be detected. For example, symptoms of pulmonary fibrosis include, but are not limited to shortness of breath, cough, and diminished exercise tolerance.

As used throughout, by subject is meant an individual. Preferably, the subject is a mammal such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical formulations are contemplated herein.

As used throughout, a proline-glycine-proline (PGP)-containing peptide can be a peptide of about three to about twenty amino acids in length that comprises PGP. For example, the peptide can be about three, four, five, six, seven, eight, nine, ten, eleven, twelve, thirteen, fourteen, fifteen, sixteen, seventeen, eighteen, nineteen or twenty amino acids in length. The peptide can also be about three to about ten amino acids in length, about three to about twelve amino acids in length, about three to about fifteen amino acids in length, or about three to about eighteen amino acids in length. The peptides can be N-acetylated or non-N-acetylated. See, for example, Haddox et al. *Invest. Ophthalmol. Vis. Sci.* 40(10):2427-2429 (1999). For example, the peptide can comprise acetylated PGP (Ac-PGP or N-acetyl-PGP) or non-acetylated PGP (PGP). The peptide can also be a non-naturally occurring peptide comprising PGP. For example, the PGP-containing peptide can be a polymer comprising one or more PGP repeats, for example, N-(PGP)$_4$-PGLG (SEQ ID NO: 1). A peptide comprising N-(PGP)$_x$ (N-acetyl-(PGP)$_x$) or (PGP)$_x$, wherein x is 1, 2, 3, 4, 5 or greater can also be used. Any of the peptides provided herein can also be methylated and/or modified to comprise a t-Boc group. For example, the peptide can be t-Boc-PGP or t-Boc-PGP-OMe. Another non-limiting example is a peptide comprising alanine-proline-glycine-proline-arginine (APGPR) (SEQ ID NO: 2). It is understood that analogs of these peptides are also provided herein.

Also provided herein is a method of treating fibrosis or a disease associated with fibrosis in a subject. The method comprises obtaining a biological sample from the subject; determining the level of expression or activity of angiotension-converting enzyme (ACE), PGP, Ac-PGP, prolyl endopeptidase and/or a matrix metalloprotease in the sample, wherein an increase in expression or activity of ACE, a decrease in activity or expression of Ac-PGP, a decrease in activity or expression of PE and/or a decrease in activity or expression of a MMP as compared to a control indicates the subject has fibrosis or a disease associated with fibrosis; and administering a therapeutically effective amount of a PGP-containing peptide to the subject. In the methods set forth herein, the MMP can be one or more of MMP 1, 8 or 9, as these MMPs generate PGP from collagen.

Also provided is a method of treating fibrosis or a disease associated with fibrosis comprising obtaining a biological sample from the subject; determining the level of acetylation of PGP to Ac-PGP, wherein a decrease in acetylation indicates the subject has fibrosis or a disease associated with fibrosis; and administering a therapeutically effective amount of a PGP-containing peptide to the subject.

As used throughout, any biological sample can be derived from a subject. The biological sample can include, but is not limited to, a cell, tissue or biological fluid from the subject. For example, the sample can be a sample from the lung of a subject. These include, but are not limited to bronchoalveolar lavage fluids, lung tissue or lung cells isolated from lung tissue. The biological sample can also be a tissue biopsy (for example, a needle biopsy), blood or components thereof, serum, bone marrow, cerebrospinal fluid, urine, saliva, muscle, tissue infiltrate and the like. Optionally the biological sample includes cells derived from the subject and cell culture medium. Additional examples of lung samples include, but are not limited to, sputum and exhaled breath condensate.

A decrease in expression can be measured by detecting the amount of a peptide or a protein in the sample. The amount of a peptide or protein expressed in a cell, can be determined by methods standard in the art for quantitating peptides or proteins, such as densitometry, absorbance assays, fluorometric assays, Western blotting, ELISA, ELISPOT, immunoprecipitation, immunofluorescence (e.g., FACS), mass spectroscopy, immunohistochemistry, etc., as well as any other method now known or later developed for quantitating specific peptides or proteins in or produced by a cell.

A decrease in the amount of mRNA encoding prolyl endopeptidase and/or a matrix metalloprotease in a cell can be determined by methods standard in the art for quantitating nucleic acids in a cell, such as in situ hybridization, quantitative PCR, RT-PCR, Taqman assay, Northern blotting, ELISPOT, dot blotting, etc., as well as any other method now known or later developed for quantitating the amount of a nucleic acid in a cell. PE and MMP enzymatic activity can also be quantified by methods known in the art. Further, as set forth herein, ACE expression and activity can be detected. Methods for detecting and quantifying ACE are known in the art and provided in the Examples. Also, see, for example, Sentandreu and Toldra (*Nature. Protoc.* 1(5): 2423-7 (2006)).

In the methods provided herein, a decrease can be about 5%, 10%, 20%, 30%, 40%, 50%, 60%, 70%, 80%, 90%, 100% or any percentage in between as compared to a control sample or a control value. In the methods provided herein, an increase can be about 5%, 10%, 20%, 30%, 40%, 50%, 60%, 70%, 80%, 90%, 100%, 200%, 300%, 500%, 500% or greater as compared to a control sample or a control value.

Any of the methods provided herein can further comprise administering an angiotensin converting enzyme inhibitor to the subject. These include, but are not limited to, Benazepril, Captopril, Enalapril, Fosinopril, Lisinopril, Moexipril, Perindopril, Quinapril, Ramipril, and Trandolapril. Optionally, the angiotension converting enzyme inhibitor inhibitor can be an ACE N-domain selective inhibitor, such as, for example, AcSDKP (acetyl-Ser-Asp-Lys-Pro-COOH) (SEQ ID NO: 3) or RXP 407 (See Junot et al. "RXP 407, a selective inhibitor of the N-domain of angiotension I-converting enzyme, blocks in vivo degradation of hemoregulatory peptide acetyl-Ser-Asp-Lys-Pro(SEQ ID NO: 3) with no effect on angiotension I hydrolysis," *J. Pharmacol. Exp. Ther.* 297(2): 606-611 (2001)).

As used throughout, treat, treating, and treatment refer to a method of reducing or delaying one or more effects or symptoms of fibrosis in, for example, a subject diagnosed with fibrosis. Treatment can also refer to a method of reducing the underlying pathology rather than just the symptoms. The effect of the administration to or treatment of the subject can have the effect of, but is not limited to, reducing one or more symptoms of the disease or disorder, a reduction in the severity of the disease or disorder, the complete ablation of the disease or disorder, or a delay in the onset or worsening of one or more symptoms. For example, a disclosed method is considered to be a treatment if there is about a 10% reduction in one or more symptoms of the disease in a subject when compared to the subject prior to treatment or when compared to a control subject or control value. Thus, the reduction can be about a 10, 20, 30, 40, 50, 60, 70, 80, 90, 100%, or any amount of reduction in between.

As used herein, by prevent, preventing, or prevention is meant a method of precluding, delaying, averting, obviating, forestalling, stopping, or hindering the onset, incidence, severity, or recurrence of fibrosis. For example, the disclosed method is considered to be a prevention if there is a reduction or delay in onset, incidence, severity, or recurrence of fibrosis or one or more symptoms of in a subject susceptible to fibrosis as compared to control subjects, for example, a control subject susceptible to fibrosis that did not receive a PGP-containing peptide. The disclosed method is also considered to be a prevention if there is a reduction or delay in onset, incidence, severity, or recurrence of fibrosis or one or more symptoms of fibrosis in a subject susceptible to fibrosis after receiving a PGP-containing peptide as compared to the subject's progression prior to receiving treatment. Thus, the reduction or delay in onset, incidence, severity, or recurrence of fibrosis can be about a 10, 20, 30, 40, 50, 60, 70, 80, 90, 100%, or any amount of reduction in between.

The agents described herein can be provided in a pharmaceutical composition. These include, for example, a pharmaceutical composition comprising a therapeutically effective amount of as PGP-containing peptide and a pharmaceutical carrier. The composition can further comprise a therapeutically effective amount of an ACE inhibitor. Optionally, the ACE inhibitor can be non-naturally occurring. The compositions described herein can be in a container, for example, and not to be limiting, a nasal sprayer, a nebulizer or an inhaler.

Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the agent described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected agent without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 22nd edition, Loyd V. Allen et al, editors, Pharmaceutical Press (2012)

Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the agent(s) described herein suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof are admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butylenegly-col, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Administration can be carried out using therapeutically effective amounts of the agents described herein for periods of time effective to treat fibrosis. The effective amount can be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to about 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day.

According to the methods taught herein, the subject is administered an effective amount of the agent. The terms effective amount and effective dosage are used interchangeably and refer to any amount necessary or sufficient to produce a desired physiologic response. Effective amounts and schedules for administering the agent can be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the activity of the specific compound employed, the metabolic stability and length of action of that compound, the species, age, body weight, general health, sex and diet of the subject, the mode and time of administration, rate of excretion, drug combination, and severity of the particular condition and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

The compositions are administered in a number of ways depending on whether local or systemic treatment is desired, and on the area to be treated. The compositions are administered via any of several routes of administration, including topically, orally, parenterally, intravenously, intra-particularly, intraperitoneally, intramuscularly, subcutaneously, intracavity, transdermally, intrahepatically, intracranially, nebulization/inhalation, or by installation via bronchoscopy.

Optionally, the composition is administered by oral inhalation, nasal inhalation, or intranasal mucosal administration. Administration of the compositions by inhalant can be through the nose or mouth via delivery by spraying or droplet mechanism. For example, in the form of an aerosol inhalant, a nasal spray or a nebulizer solution. Effective doses for any of the administration methods described herein can be extrapolated from dose-response curves derived from in vitro or animal model test systems.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Example 1

As PGP and Ac-PGP are collagen by-products, they can be detected in the lungs of patients with neutrophilic lung diseases like chronic obstructive pulmonary disease (COPD). However, when BALF from patients with IPF was examined, no Ac-PGP was found and low amounts of PGP were found. BALF from bleomycin-exposed mice were examined, and again, no PGP or Ac-PGP could be detected. Furthermore, BALF from bleomycin-exposed mice degraded Ac-PGP while control BALF did not, potentially explaining the absence of Ac-PGP. The Ac-PGP degrading protease was identified as angiotensin converting enzyme (ACE). Intra-tracheal administration of Ac-PGP to bleomycin-exposed mice abrogated pulmonary fibrosis dose-dependently while non-acetylated PGP had a partial effect and a control peptide (PGG) was ineffective. Thus, absence of Ac-PGP in pulmonary fibrosis contributes to disease. BALF from IPF patients contained higher ACE levels and activity compared with BALF from healthy controls and COPD patients. Thus, degradation of Ac-PGP by ACE could contribute to fibrosis in IPF. Also, Ac-PGP inhibited myofibroblast differentiation and pro-fibrotic functions in vitro. Based on the results provided herein, Ac-PGP prevents fibrosis through inhibiting myofibroblasts and Ac-PGP breakdown by ACE underlies the persistent myofibroblast activity that underlies IPF and other fibrotic diseases. Consequently, administration of Ac-PGP or other-PGP containing peptides or inhibiting ACE provides a novel therapy for pulmonary fibrosis.

As shown in FIG. 1, in acute lung injury, neutrophils generate Ac-PGP from collagen to propagate inflammation. Ac-PGP inhibits myofibroblasts and must be cleared by macrophage and myofibroblast-derived ACE to allow repair to start. Clearance of Ac-PGP by ACE may help prevent chronic inflammation and the pathologic fibrosis that accompanies it. During resolution, Ac-PGP is generated from newly-synthesized collagen, likely by myofibroblasts, and ACE activity diminishes. Ac-PGP feeds back to inhibit myofibroblasts and prevent further collagen deposition. In this way, ACE and Ac-PGP orchestrate repair. Perturbations of this pathway can lead to disease as not enough Ac-PGP and too much ACE causes excess fibrosis, as in IPF, and the opposite causes loss of matrix as in COPD.

BALF from Bleomycin-Exposed Mice Degrades Ac-PGP

Figure 2A:
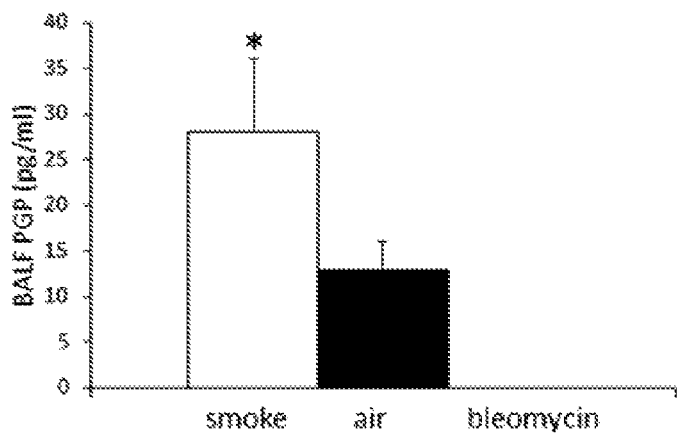
FIG. 2A shows that (bronchoalveolar lavage fluid) BALF from mice collected after bleomycin exposure contain no PGP or Ac-PGP; *smoke vs air-exposed.
Figure 2B:
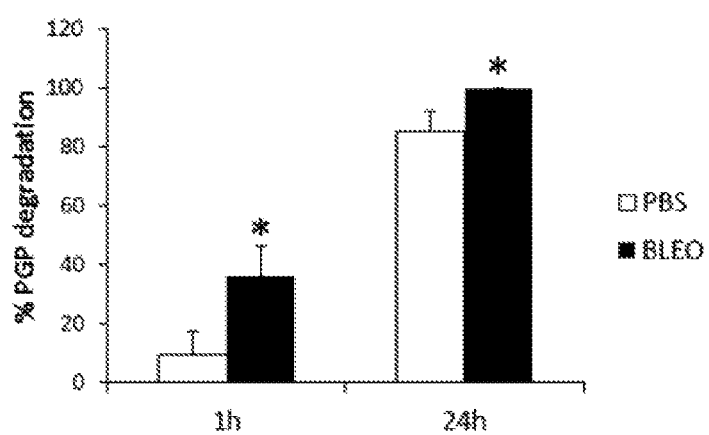
FIG. 2B shows that BALF from bleomycin-exposed mice degrade PGP faster than controls; *bleo vs control at 1 h and 24 h.
Figure 2C:
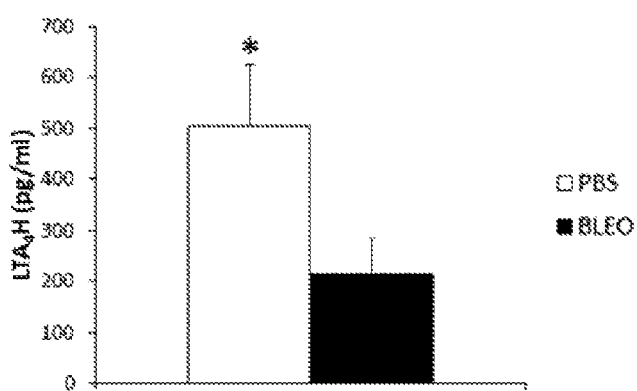
FIG. 2C shows that BALF from bleomycin-exposed mice contain less $LTA_4H$ than controls.
Figure 2D:
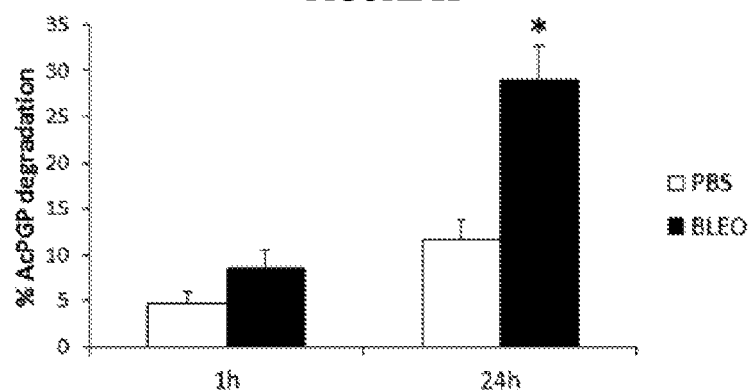
FIG. 2D shows that BALF from bleomycin-exposed mice degrade Ac-PGP whereas controls do not; *bleo vs control at 24 h.
Figure 2E:
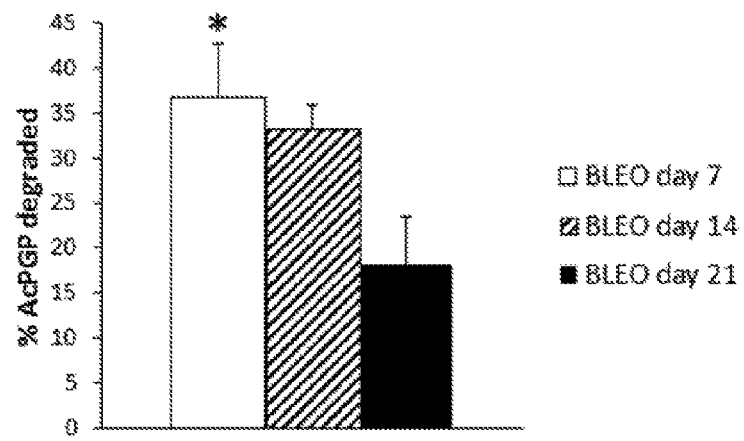
FIG. 2E shows that Ac-PGP degrading activity in BALF from bleomycin-exposed mice declines 21 days after exposure; *day 7 vs day 21.

BALF was obtained from bleomycin-exposed mice 7, 14 and 21 days after exposure and analyzed for PGP and Ac-PGP by electrospray ionization-liquid chromatography-mass spectrometry/mass spectrometry (ESI-LC-MS/MS), expecting to find high levels of these peptides due to the extensive collagen generation and remodeling that occurs in the lungs of these mice. Surpisingly, no PGP or Ac-PGP was found at any time point. This is the opposite of what was seen in mice exposed to smoke and LPS where large amounts of Ac-PGP and PGP were generated (FIG. 2A). Absence of PGP and Ac-PGP from BALF of bleomycin-exposed mice could be due to lack of generation or excess breakdown of these peptides. Accordingly, BALF from bleomycin-exposed mice was incubated with 100 μg/ml PGP or Ac-PGP and breakdown of these peptides was measured by ESI-LC-MS/MS after one and 24 hours. Control and bleomycin-exposed mouse BALF degraded PGP but the rate of degradation was faster in bleomycin-exposed mice (FIG. 2B). PGP is broken down in the lung by leukotriene $A_4$ hydrolase ($LTA_4H$). However, less $LTA_4H$ was found in bleomycin-exposed mouse BALF than in controls (FIG. 2C). Bleomycin-exposed mouse BALF degraded Ac-PGP after 24 hours, whereas control BALF did not (FIG. 2D), confirming that another peptidase is responsible, as $LTA_4H$ cannot degrade Ac-PGP. Ac-PGP breakdown by BALF was greatest 7 and 14 days after bleomycin exposure and declined at 21 days (FIG. 2E). This suggests that Ac-PGP degrading activity in BALF is related to fibrosis as collagen synthesis in bleomycin-exposed lungs declines after 14 days. Ac-PGP appears to be the critical peptide as control BALF cannot degrade it. To determine if absence of Ac-PGP contributes to fibrosis, Ac-PGP in the lungs of bleomycin-exposed mice was replaced and its effects were quantified.

Example 2

Ac-PGP Abrogates Bleomycin-Induced Pulmonary Fibrosis in Mice

Figure 3:
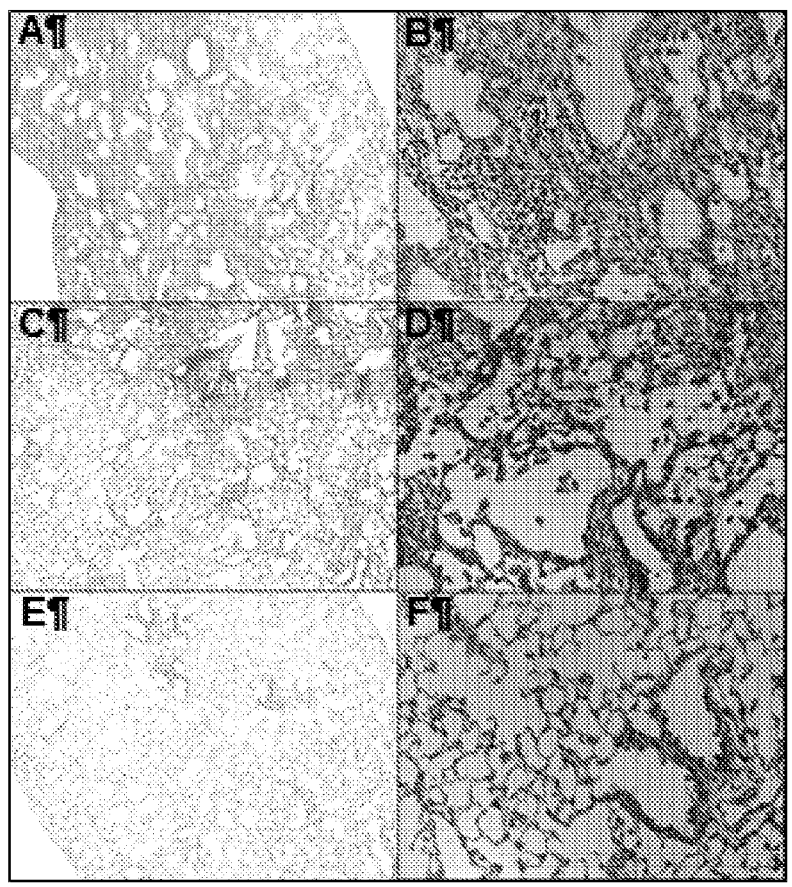
FIGS. 3A-F show H&E staining of lung tissue from C57B16 mice. C57B16 mice treated with Ac-PGP 250 μg IT daily for two weeks starting 7 days after bleomycin exposure, almost completely abrogates lung fibrosis (FIGS. 3E, F) as compared to PBS-treated controls (FIGS. 3A, B). Ac-PGP 125 μg per day had an intermediate effect (FIGS. 3C,D). A, C, E (5×); B, D, F (20×).
Figure 4:
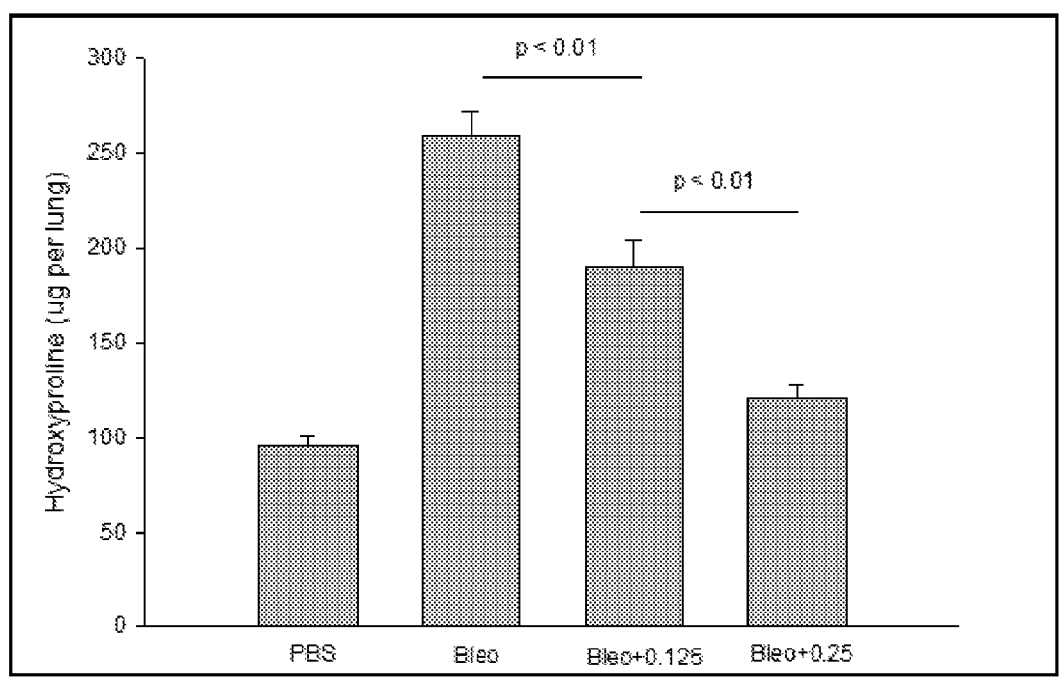
FIG. 4 shows that administration of Ac-PGP 250 μg intratracheally (IT) daily for two weeks starting at day 7 (Bleo+0.25) almost completely abrogates bleomycin-induced lung fibrosis in mice measured as lung hydroxyproline compared to bleomycin-exposed, PBS-treated controls (Bleo). Ac-PGP 125 μg per day (Bleo+0.125) was about 50% effective. Mean±SEM, n=8 mice per group.
Figure 5:
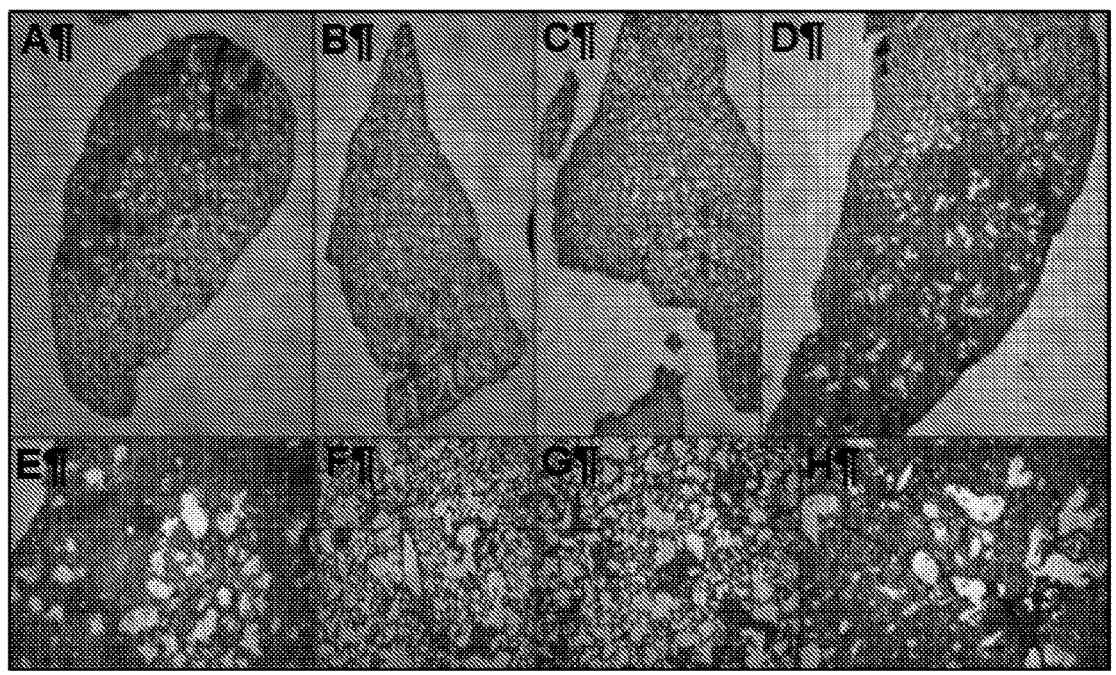
FIGS. 5A-E show the effects of administration of Ac-PGP. Administration of Ac-PGP 250 μg IT daily for 2 weeks starting at day 7 abrogates bleomycin-induced lung fibrosis in mice (FIGS. 5B, F) compared to bleomycin-exposed, PBS-treated controls (FIGS. 5A, E). PGP 250 μg per day was partially effective (FIGS. 5C, G). PGG 250 μg per day had no effect (FIGS. 5D, H). H&E staining, A-D (2×), E-H (20×).
Figure 6:
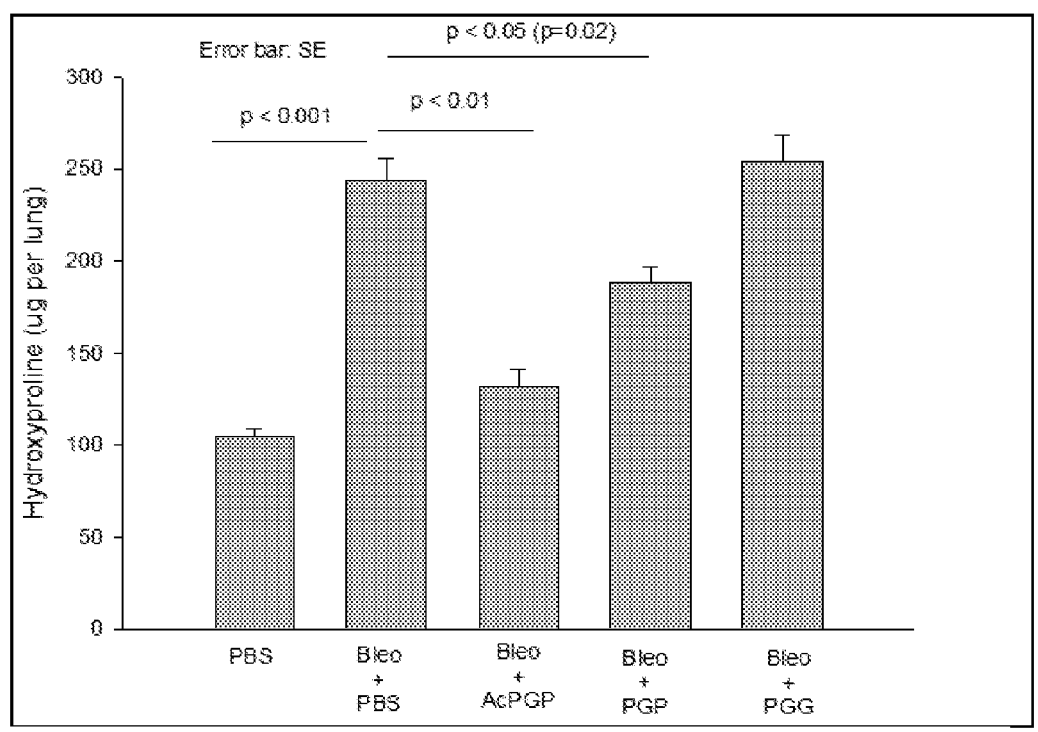
FIG. 6 shows that administration of Ac-PGP 250 μg IT daily for two weeks starting at day 7 almost completely abrogates bleomycin-induced lung fibrosis in mice measured as lung hydroxyproline compared with PBS-treated controls. PGP was less effective. PGG had no effect. Mean±SEM, n=6 mice per group

Ac-PGP was administered intratracheally (IT) daily to mice from days 7 to 21 post bleomycin exposure. Day 7 was chosen as the first day of treatment as this is when the inflammatory phase of lung injury induced by bleomycin is ending and the fibrotic/repair phase is starting. Two different doses of Ac-PGP were used: 250 μg or 125 μg per mouse per day. At day 21, Ac-PGP-treated animals were euthanized and their lungs compared with bleomycin-treated, PBS-treated controls. It was found that 250 μg of Ac-PGP per day almost completely abrogated bleomycin-induced pulmonary fibrosis on lung histology whereas 125 μg per day was about half as effective (FIG. 3). Findings on histology were confirmed with whole lung hydroxyproline measurements (FIG. 4). Bleomycin-exposed mice who received Ac-PGP failed to lose weight in contrast to bleomycin-exposed, PBS-treated mice which lost weight as expected (24±5% for PBS vs 1.3±1.2% for Ac-PGP, mean±SEM). These data show that absence of Ac-PGP in the fibrotic lung is not just an association but can be causally related to pulmonary fibrosis as replacement of Ac-PGP ameliorates it. Whether this anti-fibrotic effect was specific to Ac-PGP or a general property of proline-containing tri-peptides was tested by conducting another therapeutic trial in bleomycin-exposed mice, using the higher dose of Ac-PGP (250 μg) and expanding these treatments to include non-acetylated PGP and PGG at the same dose. It was again found that 250 μg of Ac-PGP IT daily was almost 100% effective at abrogating bleomycin-induced pulmonary fibrosis. Non-acetylated PGP was half as effective and a control peptide, PGG, had no effect (FIG. 5). These results were confirmed by whole lung hydroxyproline measurements (FIG. 6). These data confirm that the anti-fibrotic effect is specific to the PGP tripeptide with N-terminal acetylation conferring much greater potency.

Example 3

The Ac-PGP Degrading Enzyme in the Lung is ACE

Figure 7:
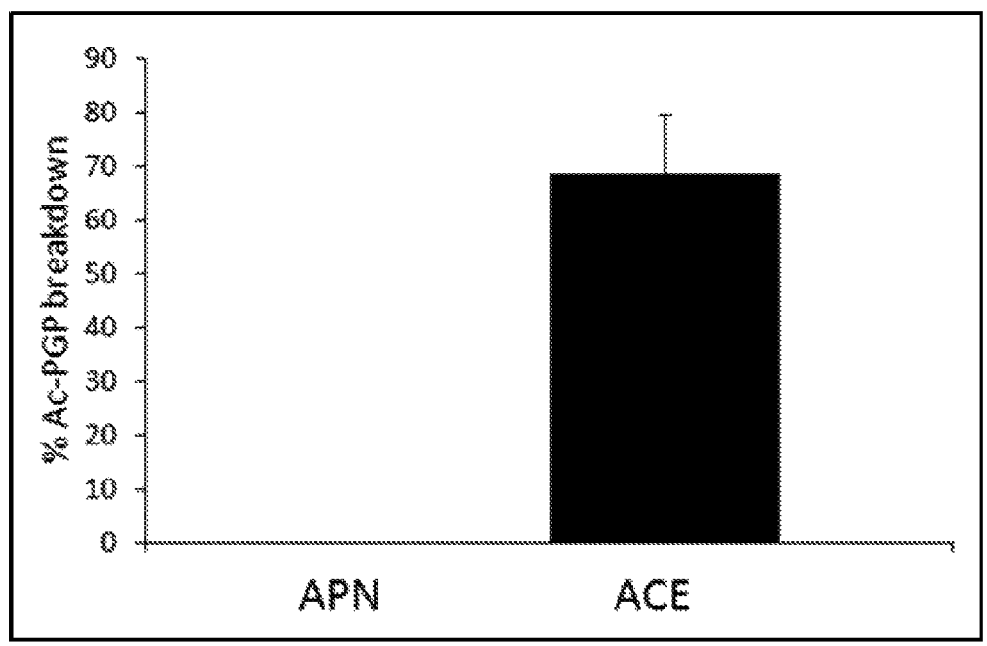
FIG. 7 shows the results of incubation of rhACE and rhAPN (1 μg/ml) with 100 μg/ml Ac-PGP×24 h. Residual Ac-PGP was measured by ESI-LC-MS/MS. ACE degraded 70% of Ac-PGP whereas APN had no activity (n=4 expts).
Figure 8:
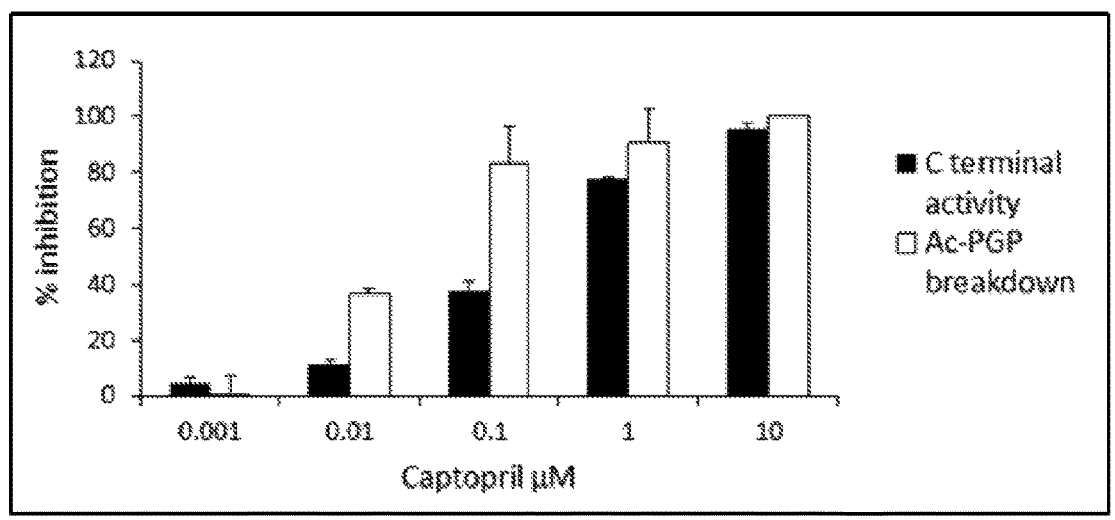
FIG. 8 shows the results of incubation of rhACE (1 μg/ml) with 100 μg/ml Ac-PGP. Residual Ac-PGP was measured. Degradation of the fluorogenic ACE substrate Mca-RPPGF-SAFK(Dnp)-OH (SEQ ID NO: 4) (R&D) by ACE was measured over ten minutes and Vmax determined. Various concentrations of captopril were added and percent inhibition calculated. Captopril had greater inhibitory effect on Ac-PGP degradation suggesting that this occurs at the N-terminal active site of ACE.
Figure 9:
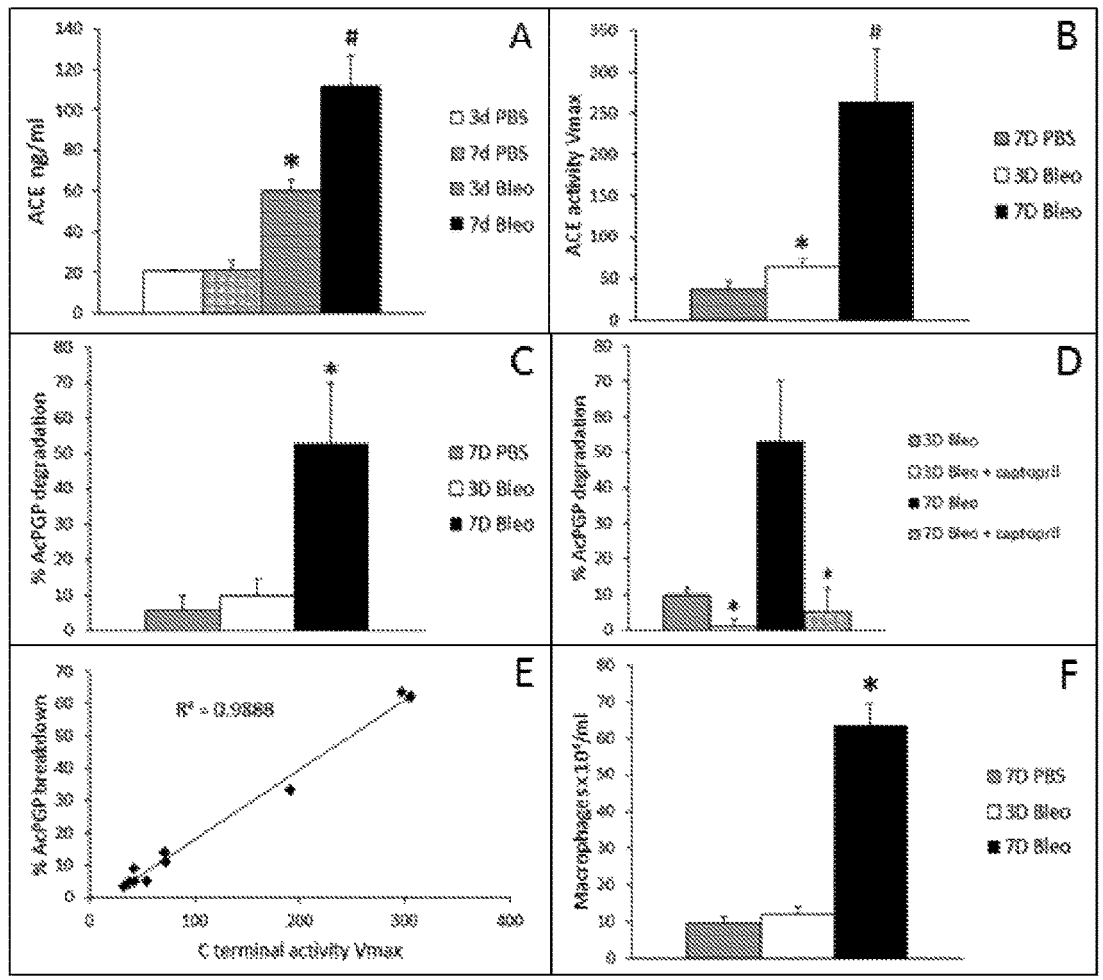
FIGS. 9A-F show Ac-PGP degrading activity. BALF was collected from mice 3 and 7 days after bleomycin exposure and assayed for ACE by ELISA. ACE activity was measured by degradation of Mca-RPPGFSAFK(Dnp)-OH (SEQ ID NO: 4) over 20 mins. and Vmax estimated from the linear part of the curve. ACE levels, as shown in FIG. 9A, and activity, as shown in FIG. 9B, were higher 3 and 7 days post bleomycin-exposure compared to PBS-exposed controls. (*p≤0.01 compared to PBS, #p≤0.01 compared to PBS and 3D bleomycin)

Studies to identify the peptidase responsible for Ac-PGP breakdown in the fibrotic lung were performed. Two candidates were tested: aminopeptidase N (APN), a ubiquitous enzyme with multiple biological effects that processes bioactive peptides, and angiotensin converting enzyme (ACE). Recombinant human (rh)APN and rhACE were incubated with Ac-PGP in vitro and Ac-PGP breakdown was measured after 24 hours. ACE degraded Ac-PGP while APN could not (FIG. 7). Further, captopril inhibition of Ac-PGP cleavage by rhACE was greater at lower concentrations than cleavage of a classic C domain ACE substrate (FIG. 8). Captopril inhibits both active sites of ACE but has greater potency (lower $K_i$) for the N domain site. Whether ACE was the peptidase responsible for Ac-PGP breakdown in the bleomycin model was investigated. BALF was obtained from mice three and seven days after bleomycin exposure as Ac-PGP degrading activity in BALF is maximal at seven days (FIG. 2E). BALF were assayed for ACE by ELISA and activity. ACE protein and activity increase three days post bleomycin exposure and even more after seven days compared to PBS-exposed controls (FIGS. 9A, B). Ac-PGP degrading activity in BALF increased at the same time (FIG. 9C). Ac-PGP degradation by BALF was abolished by addition of 1 μM captopril (FIG. 9D). ACE C domain and Ac-PGP degrading activities in BALF were tightly correlated (FIG. 9E). These data provide strong evidence that the Ac-PGP degrading activity present in bleomycin-exposed mouse BALF is due to ACE. By day 7, macrophages increase dramatically in BALF (FIG. 9F). These are a likely source of ACE as macrophages and myofibroblasts express renin and ACE and generate ATII in early fibrosis.

Example 4

BALF from IPF Patients Contains No Ac-PGP and High Levels of ACE

Figure 10:
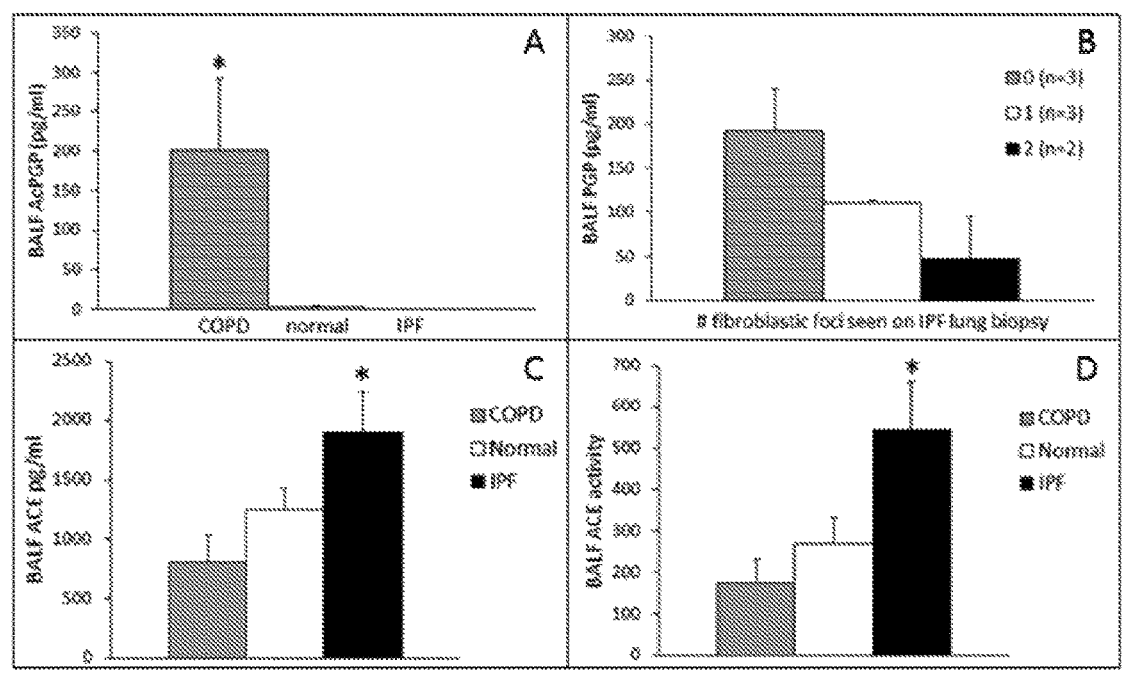
FIG. 10A shows the results of BALF from human patients assayed for Ac-PGP by ESI-LC-MS/MS. BALF from COPD patients (n=5) contained more Ac-PGP than controls (n=18, *p≤0.01). IPF BAL fluids (n=16) contained no Ac-PGP.
FIG. 10B shows that BALF PGP in IPF trended lower with more fibroblastic foci seen on lung biopsy (n=8).
FIG. 10C shows that ACE levels in IPF BALF were higher in IPF (n=9) than in COPD (n=17, *p=0.02). The difference with controls was not significant.
FIG. 10D shows that ACE activity in human BALF, measured by degradation of Mca-RPPGFSAFK(Dnp)-OH over 2 hours and expressed as fluorescence units was significantly higher in IPF BALF (n=9), compared with COPD (n=17, *p<0.01) and controls (n=16, *p<0.05). Data presented as mean±SEM.

BALF from human patients with IPF contained no Ac-PGP. Low levels of PGP were present which trended lower with higher fibrosis scores, available in eight subjects (FIGS. 10A, B). Levels of ACE protein in IPF BALF were higher than in COPD. There was a trend to higher levels in IPF BALF than in controls. ACE activity in IPF BALF was higher than both controls and COPD (FIGS. 10C, D). These data show that over-activity of ACE can play a role in human IPF by degrading Ac-PGP.

Figure 11:
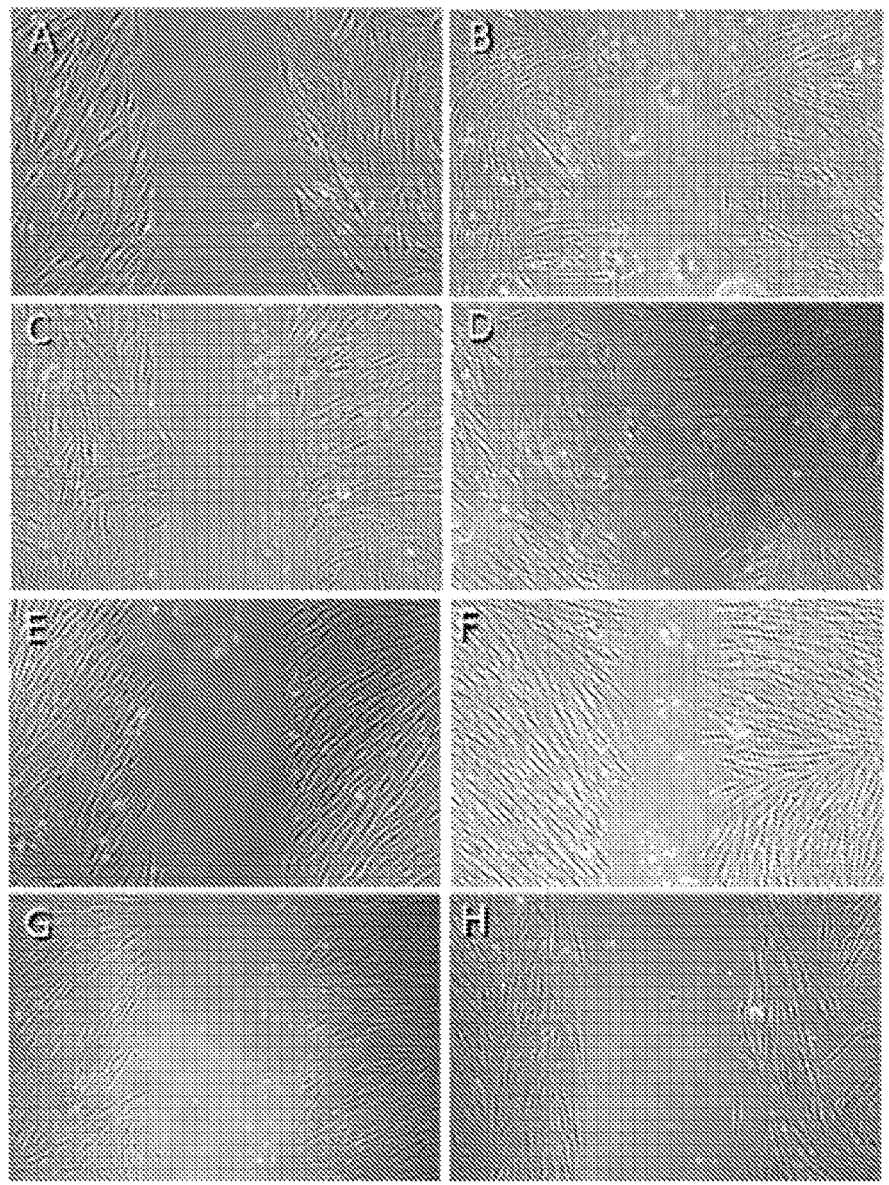
FIGS. 11A-H show IMR-90 fibroblasts under different conditions. IMR-90 fibroblasts were grown to 80-90% confluence (A, C) and differentiated to myofibroblasts with TGF-$\beta_1$ (E, G). A scratch was made and 100 µM Ac-PGP was added to some cells (FIGS. 11C, G). 48 h later, un-differentiated fibroblasts migrated across the wound (FIG. 11B) and Ac-PGP did not affect this (FIG. 11D). However, migration of myofibroblasts (FIG. 11F) by 48 h was markedly reduced by Ac-PGP (FIG. 11H).
Figure 12:
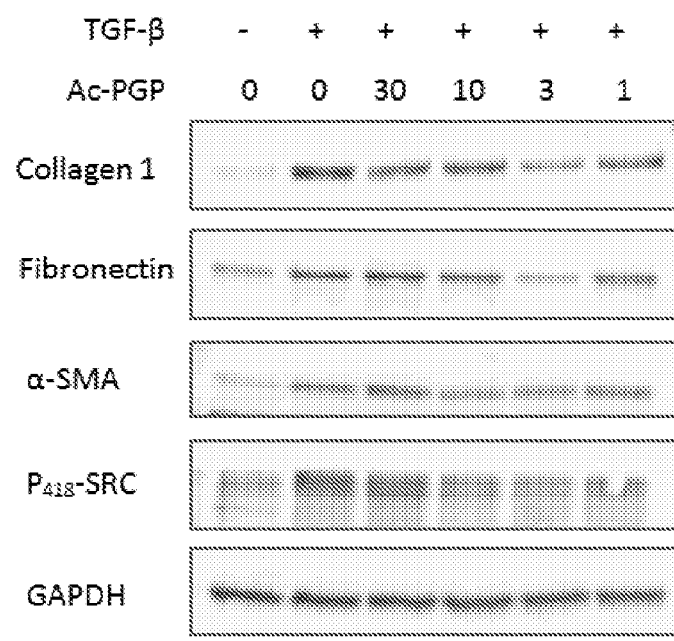
FIG. 12 shows that Ac-PGP reduces collagen, fibronectin and α-SMA expression and SRC phosphorylation in myofibroblasts. IMR-90 fibroblasts were differentiated to myofibroblasts with TGF-β 2.5 ng/ml. Ac-PGP at differing concentrations (0, 1, 3, 10 and 30 µg/ml) was added at the same time. Whole cell lysates were obtained after 48 h and probed by WB for the indicated proteins.

As shown above in FIG. 3, administration of Ac-PGP to mouse lungs results in dramatic inhibition of fibrosis (FIG. 3). The simplest explanation for this is a direct effect of Ac-PGP on the myofibroblast, altering its phenotype to stop or perhaps reverse fibrosis. In support of this idea, Ac-PGP inhibited migration by myofibroblasts but not fibroblasts (FIG. 11), suggesting that specific features of the myofibroblast phenotype render it susceptible to inhibition by Ac-PGP. Human lung fibroblasts were co-incubated with TGF-β and Ac-PGP and the effects on matrix generation and markers of MF activation and differentiation were observed. It was found that Ac-PGP reduced expression of collagen, fibronectin and α-SMA and phosphorylation of SRC by 48 hours after differentiation to myofibroblasts by TGF-β (FIG. 12). Interestingly, the greatest inhibition of myofibroblasts was seen at a dose of 3 µg/ml of Ac-PGP with lesser effects seen at 30 and 10 µg/ml, suggesting that Ac-PGP could have different effects on myofibroblasts at higher doses. Nonetheless, these data support a direct effect of Ac-PGP on myofibroblasts to inhibit differentiation and matrix protein production.

Example 5

Pro-Fibrotic Functions of Fibroblasts and Myofibroblasts

The ability of fibroblasts and myofibroblasts to perform pro-fibrotic functions and measure the activity of signaling pathways important in myofibroblast differentiation can be assessed. The effect of Ac-PGP, at various concentrations, on differentiation, pro-fibrotic functions and signaling pathways, added before, during or at various times after differentiation with TGF-$β_1$, can be determined. Migration and contractility are pro-fibrotic functions enabling myofibroblasts to enter and close a wound. Invasiveness is a feature of myofibroblasts isolated from patients with fibrotic disease, including IPF. Migration can be assessed using wound assays, and chemotaxis chambers in response to chemoattractant factors such as TGF-$β_1$ and platelet-derived growth factor. Invasiveness and contractility can be assessed using 3D collagen gels.

The effect of Ac-PGP on myofibroblast differentiation by TGF-$β_1$ can be examined. Differentiated myofibroblasts express alpha smooth muscle actin (α-SMA), which confers contractility and express collagen and ED-A fibronectin. Expression of these proteins can be assessed by real-time PCR, Western blotting (WB) and ELISA in cell lysates and culture media. Fibroblasts/myofibroblasts can be examined by immunofluorescence microscopy (IF) for differentiation markers, such as α-SMA containing stress fibers and focal adhesions by staining for vinculin. Differentiation and activation of myofibroblasts occur through Smad and non-Smad pathways. Ligation of the TGF-$β_1$ receptor phosphorylates Smad 2/3 proteins which translocate to the nucleus to initiate transcription. Adhesion, integrin activation, mechanical stimuli and growth factors, including TGF-$β_1$, activate FAK and RhoA which mediate myofibroblast differentiation, adhesion, migration and contraction through downstream effectors such as myosin light chain kinase (MLCK). Activation of these pathways can be assessed by Western blot and immunofluorescence for phosphorylation and location of the relevant proteins, and assays for FAK and RhoA activity.

It is not known what happens to myofibroblasts once repair is completed. It is possible that Ac-PGP can terminate fibrosis by inducing myofibroblast apoptosis. This idea can be tested by exposing myofibroblasts to Ac-PGP and examining them for apoptosis by terminal deoxynucleotidyl transferase Dutp nick end labeling (TUNEL), activation of caspases 3, 8 and 9 and mitochondrial release of cytochrome. $^3$H thymidine incorporation can be used to examine if Ac-PGP affects proliferation of myofibroblasts and fibroblasts, which is influenced by extracellular collagen.

It is likely that Ac-PGP will inhibit the ability of myofibroblasts to perform pro-fibrotic functions, inhibit myofibroblast differentiation, as already shown (FIG. 12) and reduce collagen production. If differentiation is inhibited signaling pathways are expected to be involved. For example, this action can involve Smad-dependent or independent pathways (FAK, RhoA) that are constitutively activated in myofibroblasts. Loss of myofibroblast phenotype without evidence of apoptosis could indicate de-differentiation.

Example 6

Myofibroblasts and Ac-PGP

Figure 13:
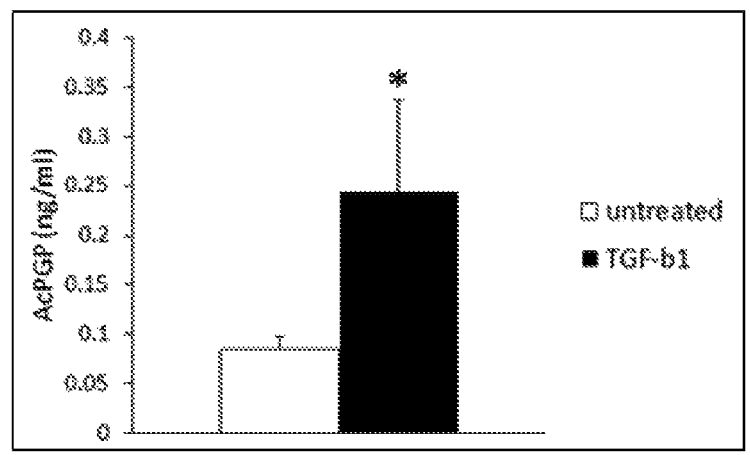
FIG. 13 shows that differentiation by TGF-$\beta_1$ increased intracellular Ac-PGP. IMR-90 fibroblast cell lysates were assayed for Ac-PGP by ESI-LC-MS/MS. Differentiation by TGF-$\beta_1$ increased intracellular Ac-PGP×3. *p<0.05.
Figure 14:
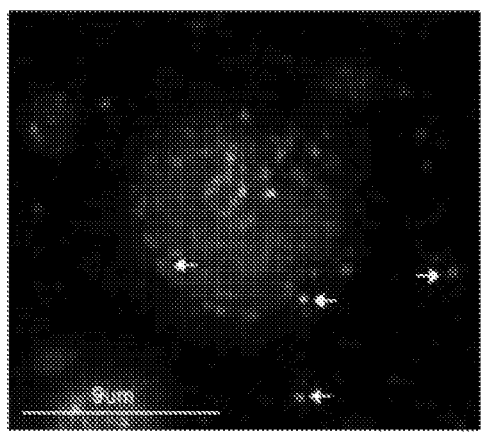
FIG. 14 shows that human PBMC contain Ac-PGP which co-localizes with PE (arrows).

Well-described pathways of collagen internalization and degradation exist within fibroblasts. Based on the results provided herein, it is likely that myofibroblasts generate Ac-PGP intracellularly from collagen in late repair to prevent persistent myofibroblast activation and pathological fibrosis. In support of this idea, human fibroblasts contain Ac-PGP, which increases after differentiation to myofibroblasts, and is likely derived from newly synthesized collagen (FIG. 13). Primary human peripheral blood mononuclear cells (PBMC) contain Ac-PGP which co-localizes with PE, suggesting in situ Ac-PGP generation (FIG. 14).

Figure 15A:
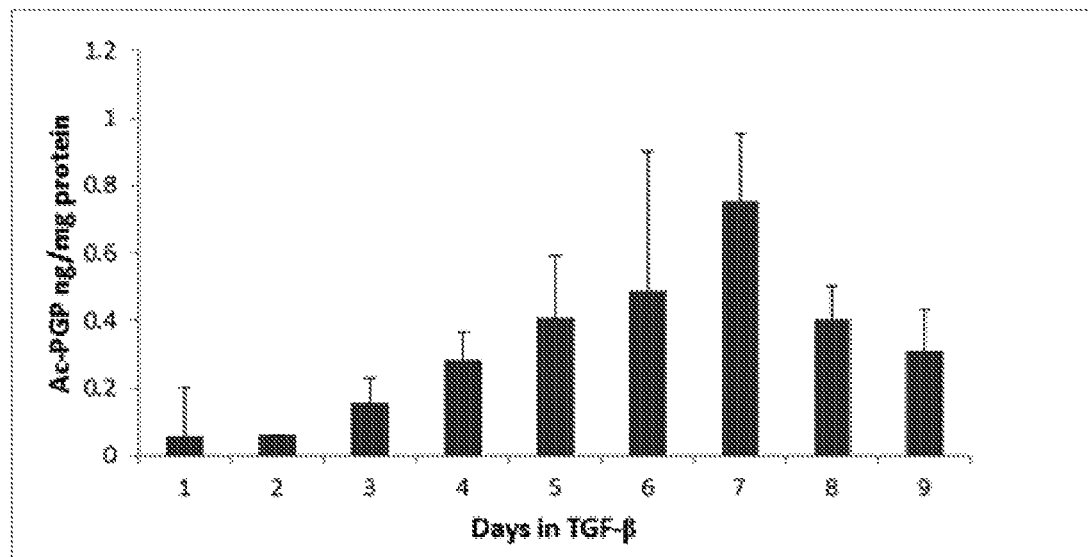
FIGS. 15A and 15B show the effects of TGF-β on Ac-PGP and PGP production in IMR-90 fibroblasts. IMR-90 fibroblasts were grown to confluence, activated with TGF-β 2.5 ng/ml and cultured for nine days. Myofibroblasts were harvested daily, homogenized, filtered and analyzed for Ac-PGP and PGP by ESI-LC-MS/MS (A). Cell growth medium was collected and assayed similarly (B).
Figure 15B:
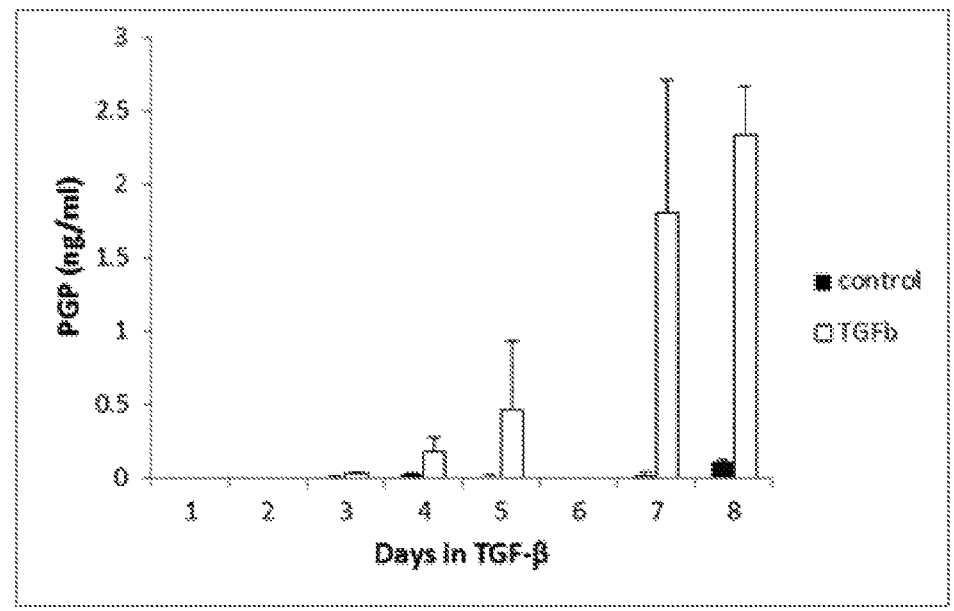

In order to determine if myofibroblasts generate Ac-PGP from newly synthesized collagen, which feeds back to inhibit their function and terminate repair, fibroblasts were differentiated to myofibroblasts with TGF-$β_1$ and cultured over several days. FIGS. 15A and 15B demonstrate that Ac-PGP and PGP levels in MF cultures increased markedly from 0.05 to 0.75 ng/mg protein by day 7 post-differentiation, thereafter falling. It is likely, based on current understanding of collagen degradation by MF, that these high levels of Ac-PGP are generated from newly synthesized collagen. Ac-PGP was found exclusively within the cell, suggesting that it is generated from lysosomal degradation pathways, possibly involving autophagy. No PGP was detected within myofibroblasts indicating that all PGP within cells is acetylated. In contrast, no Ac-PGP and high levels of PGP were detected outside myofibroblasts. PGP increased in culture medium from barely detectable levels (40 pg/ml) to 2.5 ng/ml by day eight while levels in fibroblast cultures (control) remained low (FIG. 15B). PGP detected extracellularly may be exported from the MF or generated by breakdown of secreted collagen. This PGP could act to inhibit neighboring MF in an autocrine or paracrine fashion.

Fibroblasts internalize collagen through the cell surface receptors, $α_2β_1$ integrin and urokinase-type Plasminogen Activator Receptor Associated Protein (uPARAP). Collagen is trafficked to lysosomes where it is degraded by cysteine proteases and likely PE and perhaps acetylated. Given the results set forth above, the receptors implicated in collagen endocytosis ($\alpha_2\beta_1$ integrin, uPARAP) can be blocked using specific antibodies or by using fibroblasts deficient in these receptors. The pathway of lysosomal collagen degradation can be blocked using inhibitors of cathepsins and lysosomal acidification, which are known to inhibit intracellular collagen degradation, and the cell-permeant PE inhibitor, S17092. The effects of these interventions on myofibroblast differentiation and phenotype can be examined. Experiments in human cell lines can be confirmed in primary mouse and human fibroblasts.

It is expected that collagen expression within myofibroblasts and in culture media will increase over time and that levels of Ac-PGP will increase within myofibroblasts due to increased internalization and degradation of collagen. As levels of Ac-PGP increase, it is expected that myofibroblasts will lose differentiation markers and revert to a quiescent state or undergo apoptosis. Blocking the internalization and/or degradation of collagen by myofibroblasts will likely reduce or abolish Ac-PGP generation and lead to persistent myofibroblast activation.

Example 7

Involvement of Ac-PGP and ACE in Controlling Repair in an Experimental Model of Lung Fibrosis Administration of Ac-PGP to bleomycin-exposed mice starting seven days after bleomycin exposure greatly reduces fibrosis (FIGS. 3 and 4). This is likely due to a direct effect on myofibroblasts. Examination of whole lung and isolated myofibroblasts from bleomycin-exposed, Ac-PGP treated mice can provide important information as to how Ac-PGP inhibits fibrosis.

In order to assess the effects on myofibroblasts, C57BL/6 mice can be exposed to bleomycin and treated with IT Ac-PGP 250 μg daily or PBS from days 7 to 21 post bleomycin. Mice can be sacrificed on day 21, lungs can be formalin-fixed and paraffin-embedded for histological analysis; whole lung homogenates can be prepared for hydroxyproline and RNA and protein for analyses of pro-fibrotic biomarkers. Specific measures can include H&E staining for gross histopathology; Masson's trichrome staining for collagen content and distribution; immunohistochemistry to determine the distribution/co-localization of α-SMA as a marker for myofibroblasts; hydroxyproline content for total lung collagen; real-time_PCR and WB for α-SMA, Col1A1, Col1A2 and fibronectin. Lung sections will be examined for apoptotic cells by TUNEL and stained for cleaved caspase-3. Lung fibroblasts/myofibroblasts can be isolated and assessed for pro-fibrotic functions and for the differentiated phenotype. Activation of signaling pathways of myofibroblast differentiation (FAK, RhoA) can be assessed in lung fibroblasts/myofibroblasts and in whole lung by IHC and WB for phosphorylated proteins.

Daily administration of Ac-PGP to bleomycin-exposed mice could reduce lung fibrosis before and reduce the number and activation of myofibroblasts. It is expected that fibroblasts/myofibroblasts isolated from bleomycin-exposed, Ac-PGP mice treated will have impaired functions such as contraction and motility compared to bleomycin-exposed, PBS-treated controls and less expression of pro-fibrotic biomarkers.

Example 8

Role of Ac-PGP Degradation by ACE in Promoting Fibrosis in Experimental Models of Lung Fibrosis Ac-PGP, a myofibroblast inhibitor, is likely degraded by macrophage and myofibroblast-derived ACE soon after lung injury to allow repair to begin. Myofibroblasts express all components of the ACE system and expression increases in fibrotic disease and after stimulation of fibroblasts with TGF-$\beta_1$. In late repair, Ac-PGP reappears through degradation of newly synthesized collagen and perhaps through down-regulation of ACE as well (FIG. 2E). This restores an environment where myofibroblasts are inhibited and fibrosis terminated or reversed.

Experiments can be conducted to determine if myofibroblast-derived ACE degrades Ac-PGP to allow repair to begin after acute lung injury. Studies can also be performed to determine if, in late fibrosis, Ac-PGP levels increase to inhibit myofibroblasts and prevent pathological fibrosis.

As bleomycin exposure of mice results in marked acute lung injury, it is expected that Ac-PGP can be detected in BALF early, before ACE appears by day 3 to degrade it (FIG. 9A-D). Mice can be exposed to bleomycin. Then, BALF and lung tissue can be obtained one, seven and 28 days after exposure. BALF can be analyzed for PGP and Ac-PGP by ESI-LC-S/MS, levels and activity of the PGP generating enzymes MMPs-8 and 9 and PE, ability to generate Ac-PGP ex vivo from collagen, ACE levels and activity, Ac-PGP degrading activity and cell counts and differential. BALF cells can also be examined for ACE expression by IF and differential centrifugation followed by Western blotting. BALF cell lysates can be examined for ACE activity and Ac-PGP degrading activity. Lung sections can be examined by H&E, Masson's trichrome for collagen and IHC for α-SMA and ACE. Lung tissue homogenates can be analyzed for Ac-PGP, ACE and Ac-PGP degrading activity. Lung fibroblasts/myofibroblasts can be isolated and examined for ACE expression, location and activity, Ac-PGP degrading activity and PGP/Ac-PGP by ESI-LC-MS/MS and IF using an antibody to Ac-PGP. These methods will also allow determination of the location of ACE and Ac-PGP within cells.

Levels of PGP, Ac-PGP and PGP-generating enzymes in BALF will likely be increased immediately after bleomycin exposure. Lung sections could reveal acute lung injury and BALF cells could be mostly neutrophils. It is not expected that ACE will be seen in BALF or lung tissue at this stage. By day 7 after bleomycin exposure, high levels of ACE and Ac-PGP degrading activity, inhibited by captopril, are expected in BALF. Ac-PGP will likely be absent. Large numbers of macrophages in BALF expressing ACE are expected. Lung sections could reveal collagen deposition and α-SMA and ACE expressing cells. Lung fibroblasts/myofibroblasts could express ACE and Ac-PGP degrading activity, inhibited by captopril. Despite this, it is expected that myofibroblasts will contain low levels of Ac-PGP generated as a byproduct of collagen synthesis (FIG. 13). It is expected that lung tissue, fibroblasts/myofibroblasts and perhaps BALF will show higher levels of Ac-PGP generated from collagen either phagocytosed or synthesized within the cell but not secreted.

Example 9

ACE Inhibition or Deficiency Protects Against Fibrosis Through Persistence of Ac-PGP The ACE inhibitor captopril reduces fibrosis in the bleomycin model but ATII antagonists have failed to do so consistently. Captopril can be administered to mice starting two days before bleomycin-exposure. Mice will be euthanized two weeks after exposure and their lungs examined. Levels of Ac-PGP can be measured in lungs and BALF. Similar experiments can be conducted in ACE deficient mice (Jax#002679) and in mice selectively deficient in the C or N domain active site of ACE. S-17092 can be administered to mice starting two days before bleomycin exposure and the effects on lung fibrosis and Ac-PGP expression examined. It is expected that treatment with captopril and knockout of ACE or of the N domain active site will abrogate fibrosis in the bleomycin model and that this will be accompanied by persistence of Ac-PGP in lung tissue and BALF to inhibit fibrosis. S-17092 could reduce Ac-PGP levels and restore fibrosis. It is expected that that knockout of the C domain active site will not reduce fibrosis.

Example 10

Association of Lung Expression of ACE and Ac-PGP with Disease Severity and/or Progression in IPF In preliminary experiments, it was found that there are differences in BALF ACE levels and activity between patients with IPF, COPD and healthy controls. This finding suggests that ACE has relevance to a wider spectrum of lung diseases with increased activity promoting fibrosis and decreased activity promoting loss of matrix as in COPD.

It is anticipated that ACE levels and activity are higher in IPF BALF compared with healthy controls and COPD. In order to test this, patients with IPF will be recruited. COPD patients (20) and healthy controls (20) will be recruited through the UAB Lung Health Center. Current smokers will not be recruited to avoid confounding effects of smoking on ACE and Ac-PGP. IPF and COPD patients and healthy controls will undergo bronchoscopy and collection of BALF. BALF cell counts and differential will be performed and cytospins made for microscopic examination. BALF ACE levels and activity will be assessed. Ac-PGP degrading activity will be measured and inhibition by captopril tested. BALF cells will be examined for ACE by real-time PCR, WB and IF, for ACE activity and for Ac-PGP degrading activity. Ac-PGP levels in BALF and BALF cells will be measured by ESI-LC-MS/MS. BALF cells will be examined by IF using an Ab to Ac-PGP (FIG. 14).

BALF ACE levels in IPF subjects were 1904±337 pg/ml and in controls were 1251±186 pg/ml (mean±SEM, FIG. 10C) with σ=830 ng/ml and effect size of 0.79. Twenty subjects per group should be sufficient to confirm that ACE levels in IPF BALF are higher than controls (t test, 80% power, p=0.05). The effect sizes for BALF ACE activity and Ac-PGP levels and for comparisons between IPF and COPD are even greater so n of 20 per group should suffice (FIGS. 10A, D). ANOVA analysis will be performed with Bonferroni correction to determine which groups show significant differences, confirmed by t tests.

It is expected that levels of ACE mRNA, protein, activity and Ac-PGP degrading activity will be highest in IPF BALF and BALF cells and lowest in COPD with intermediate levels in healthy controls. It is expected that ACE expression and Ac-PGP will be much higher in BALF cells than in BALF with consequently greater differences between groups.

Example 11

ACE and Ac-PGP Expression in Whole Lung and Lung Myofibroblasts Predicts Severity and/or Disease Progression in a Cohort of IPF Patients Studies can be conducted to determine if expression of ACE and Ac-PGP in whole lung and lung fibroblasts/myofibroblasts is predictive of severity and/or progression of IPF.

Lung tissue will be collected from 100 IPF patients (20 per year) undergoing VATS lung biopsy or lung transplantation at UAB. Control lung tissue will be obtained from at least 50 patients (10 per year) undergoing lung resection for bronchogenic carcinoma. Tissue homogenates and sections and tissue-derived fibroblasts cultured and studied at passage 2 will be made available to investigators. ACE expression/activity and levels of Ac-PGP will be studied in control and IPF lung tissue and tissue fibroblasts/myofibroblasts as described previously. Fibroblastic foci (FF) in lung sections will be quantified with a scoring system (absent 0, mild 1, moderate 2 and marked 3). A thorough clinical assessment will be conducted of all IPF patients, including age, sex, duration of illness, smoking status, forced vital capacity (FVC), diffusing capacity for carbon monoxide ($DL_{CO}$), 6 minute walk test for distance and oxygen desaturation and ABGs. Subjects with confirmed IPF will return for a repeat clinical assessment six months later.

It is anticipated that levels of ACE expression at the mRNA and protein levels will be higher in IPF compared to control subjects and correlate with progressive decline in pulmonary functions (FVC, DLCO, 6MWT) within the IPF cohort. Higher levels of ACE expression could correlate with the age of the patient. It is expected that levels of Ac-PGP in lung tissue and fibroblasts/myofibroblasts will correlate negatively with decline in lung function in the IPF cohort. It is expected that ACE staining will localize to FF and that higher ACE-associated FF scores in IPF patients will be associated with more rapid decline.

Example 12

Use of a PGP-Containing Peptide as a Therapeutic

Ac-PGP inhibits myofibroblasts in vitro and abrogates lung fibrosis in the bleomycin mouse model likely through effects on myofibroblasts. Tissue-derived fibroblasts/myofibroblasts, cultured and studied at passage 2, from patients with IPF and controls will be provided. These will be studied for evidence of myofibroblast differentiation and pro-fibrotic functions as described above. The effect of incubation with Ac-PGP at various doses and for varying periods will be assessed on myofibroblast phenotype, functions and signaling. Ac-PGP treated fibroblasts will then be examined for evidence of apoptosis.

It is expected that fibroblasts/myofibroblasts from IPF patients will show greater evidence of myofibroblast differentiation and pro-fibrotic functions than fibroblasts from normal controls. Ac-PGP will likely reverse myofibroblast differentiation, inhibit pro-fibrotic functions and reduce expression of mesenchymal proteins. Ac-PGP will likely inhibit signaling pathways of myofibroblast differentiation, consistent with returning myofibroblasts to a quiescent state.

What is claimed is:

1. A method for reducing idiopathic pulmonary fibrosis in a subject, the method comprising administering to a subject having idiopathic pulmonary fibrosis a therapeutically effective amount of a proline-glycine-proline (PGP)-containing peptide.

2. The method of claim 1, wherein the PGP-containing peptide is selected from the group consisting of acetylated PGP (Ac-PGP), PGP, tert-butyloxycarbonyl (t-Boc) PGP, N-acetyl-PGPPGPPGPPGPPGLG (SEQ ID NO: 1) and APGPR (SEQ ID NO: 2).

3. The method of claim 1, wherein the therapeutically effective amount of the PGP-containing peptide inhibits myofibroblast activity.

4. The method of claim 1, further comprising administering to the subject an agent that inhibits angiotensin converting enzyme (ACE).

5. The method of claim 4, wherein the ACE inhibitor is administered by oral inhalation, nasal inhalation, or intranasal mucosal administration.

6. The method of claim 5, wherein the ACE inhibitor is administered orally, via an inhaler, a nebulizer or a nasal sprayer.

7. The method of claim 1, wherein the PGP-containing peptide is administered by oral inhalation, nasal inhalation, or intranasal mucosal administration.

8. The method of claim 7, wherein the PGP-containing peptide is administered via an inhaler, a nebulizer or a nasal sprayer.

\* \* \* \* \*

UNITED STATES PATENT AND TRADEMARK OFFICE
CERTIFICATE OF CORRECTION

| | |
|---|---|
| PATENT NO. | : 10,335,448 B2 |
| APPLICATION NO. | : 15/525682 |
| DATED | : July 2, 2019 |
| INVENTOR(S) | : Philip J. O'Reilly and Edwin J. Blalock |

Page 1 of 1

It is certified that error appears in the above-identified patent and that said Letters Patent is hereby corrected as shown below:

In the Specification

Column 1, Lines 16-19:
Delete "This invention was made with government support under grant number HL092296 and HL07783 awarded by the National Institutes of Health. The government has certain rights in the invention."
And insert:
-- This invention was made with government support under grant numbers HL092296 and HL077783 awarded by the National Institutes of Health. The government has certain rights in the invention. --

Signed and Sealed this
First Day of October, 2019

Andrei Iancu
*Director of the United States Patent and Trademark Office*

SEQUENCE LISTING

```
<160> NUMBER OF SEQ ID NOS: 4

<210> SEQ ID NO 1
<211> LENGTH: 16
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION

<400> SEQUENCE: 1

Pro Gly Pro Pro Gly Pro Pro Gly Pro Pro Gly Pro Pro Gly Leu Gly
1               5                   10                  15

<210> SEQ ID NO 2
<211> LENGTH: 5
<212> TYPE: PRT
<213> ORGANISM: Artificial sequence
<220> FEATURE:
<223> OTHER INFORMATION: Synthetic construct

<400> SEQUENCE: 2

Ala Pro Gly Pro Arg
1               5

<210> SEQ ID NO 3
<211> LENGTH: 4
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION

<400> SEQUENCE: 3

Ser Asp Lys Pro
1

<210> SEQ ID NO 4
<211> LENGTH: 9
<212> TYPE: PRT
<213> ORGANISM: Artificial sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: modified with Methoxy-coumarin-acetic-acid
      (MCA)
<220> FEATURE:
<221> NAME/KEY: MOD_RES
<222> LOCATION: (9)..(9)
<223> OTHER INFORMATION: modified with 2,4-Dinitrophenyl(DNP)

<400> SEQUENCE: 4

Arg Pro Pro Gly Phe Ser Ala Phe Lys
1               5
```